US009095596B2

(12) United States Patent
Grimaldi et al.

(10) Patent No.: US 9,095,596 B2
(45) Date of Patent: Aug. 4, 2015

(54) TREATMENT OF NEURODEGENERATIVE DISEASES, CAUSATION OF MEMORY ENHANCEMENT, AND ASSAY FOR SCREENING COMPOUNDS FOR SUCH

(75) Inventors: Maurizio Grimaldi, Birmingham, AL (US); Judith Varady Hobrath, Pinson, AL (US); Subramaniam Ananthan, Birmingham, AL (US); Joseph A. Maddry, Birmingham, AL (US)

(73) Assignee: Southern Research Institute, Birmingham, AL (US)

( * ) Notice: Subject to any disclaimer, the term of this patent is extended or adjusted under 35 U.S.C. 154(b) by 0 days.

(21) Appl. No.: 13/501,934

(22) PCT Filed: Oct. 14, 2010

(86) PCT No.: PCT/US2010/052624
§ 371 (c)(1),
(2), (4) Date: Jun. 6, 2012

(87) PCT Pub. No.: WO2011/047129
PCT Pub. Date: Apr. 21, 2011

(65) Prior Publication Data
US 2012/0245166 A1 Sep. 27, 2012

Related U.S. Application Data

(60) Provisional application No. 61/251,874, filed on Oct. 15, 2009.

(51) Int. Cl.
| *A61K 31/675* | (2006.01) |
| *A61K 31/427* | (2006.01) |
| *A61K 31/4402* | (2006.01) |
| *C07D 417/02* | (2006.01) |
| *C07D 417/14* | (2006.01) |
| *C07D 277/38* | (2006.01) |
| *C07D 277/20* | (2006.01) |
| *C07D 213/72* | (2006.01) |

(52) U.S. Cl.
CPC ............ *A61K 31/675* (2013.01); *A61K 31/427* (2013.01)

(58) Field of Classification Search
CPC .. C07D 417/02; C07D 417/14; C07D 277/38; C07D 277/20; C07D 213/72; A61K 31/427; A61K 31/44; A61K 31/4402
See application file for complete search history.

(56) References Cited

U.S. PATENT DOCUMENTS

| 6,277,872 | B1 | 8/2001 | Brenner et al. | |
| 2005/0227989 | A1* | 10/2005 | Wang et al. | 514/252.05 |
| 2006/0074083 | A1 | 4/2006 | Kalvinsh et al. | |
| 2006/0293329 | A1 | 12/2006 | Hogenkamp et al. | |
| 2007/0105919 | A1 | 5/2007 | Nakajima et al. | |
| 2007/0167409 | A1 | 7/2007 | Chow et al. | |

FOREIGN PATENT DOCUMENTS

| WO | WO-2005/092890 A2 | 10/2005 |
| WO | WO-2008/049864 A1 | 5/2008 |

OTHER PUBLICATIONS

Sheridan, R.P. The Most Common Chemical Replacements in Drug-Like Compounds, J. Chem. Inf. Comput. Sci., 2002, vol. 42, pp. 103-108.*

J. G. Cannon Chapter Nineteen in Burger's Medicinal Chemistry and Drug Discovery, Fifth Edition, vol. I: Principles and Practice, Wiley-Interscience 1995, pp. 783-802, 784.*

Fournier et al. "Apamin improves reference memory but not procedural memory in rats by blocking small conductance Ca2+ activated K+ channels in an olfactory discrimination task" Behavioural Brain Research, vol. 121, issue 1-2, Jun. 2001, pp. 81-83.*

Underwood, Annie "Can Memory Loss Be Prevented?" The New York Times, Jun. 11, 2009, pp. 1-3.*

Malgouris, Christiane, et al., "Riluzole, a Novel Antiglutamate, Prevents Memory Loss and Hippcampal Neuronal Damage in Ischemic Gerbils," The Journal of Neuroscience, Nov. 1989, vol. 9, No. 11, p. 3720-3727.

International Search Report and Written Opinion issued in International Application No. PCT/US2010/052624, date of mailing Mar. 1, 2011.

Manuvakhova et al., "Identification of Novel Small Molecule Activators of Nuclear Factor-?B With Neuroprotective Action Via High-Throughput Screening," Journal of Neuroscience Research 89:58-72 (2011).

Notification Concerning Transmittal of International Preliminary Report on Patentability dated Apr. 26, 2012 issued in corresponding Application No. PCT/US2010/052624.

* cited by examiner

*Primary Examiner* — Kendra D Carter
(74) *Attorney, Agent, or Firm* — Novak Druce Connolly Bove + Quigg LLP

(57) ABSTRACT

Methods for enhancing memory and/or learning and prevent neurodegeneration by administration of certain heterocyclic and aromatic compounds are described. The methods are particularly useful for treating patients suffering from a neurodegenerative disease such as (without limitation) Alzheimer's, Parkinsons's, Lou Gehrig's (ALS) disease or memory or learning impairment. A neuronal human cell-based assay that assess NF-kB gene up-regulation using a luciferase reporter is also provided that screens for compounds useful in methods for enhancing memory or learning.

6 Claims, 27 Drawing Sheets

| | |
|---|---|
| 1. | SRI # 22777 |
| 2. | SRI # 22818 |
| 3. | SRI # 22782 |
| 4. | SRI #22781 |
| 5. | SRI # 22776 |
| 6. | SRI # 22820 |
| 7. | SRI # 22775 |
| 8. | SRI # 22817 |
| 9. | SRI # 22779 |
| 10. | SRI # 22819 |
| 11. | SRI # 22772 |
| 12. | SRI # 22771 |
| 13. | SRI # 22816 |
| 14. | SRI # 22774 |
| 15. | SRI # 22780 |
| 16. | SRI # 22864 |
| 17. | SRI # 22778 |
| 18. | SRI # 22773 |

FIGURE 12

| ID | ADMET BBB (1) | BBB Level (2) | QPlogBB (3) | CNS (4) | QPPMDCK (5) | QPlogPo/w (6) | RuleOfFive (7) |
|---|---|---|---|---|---|---|---|
| SRI-22781 | -0.299 | 2 | -1.16 | -2 | 178 | 2.36 | 0 |
| SRI-22818 | 0.187 | 1 | 0.173 | 1 | 5884 | 3.87 | 0 |
| SRI-22779 | 0.18 | 1 | -0.113 | 0 | 4420 | 3.93 | 0 |
| SRI-22776 | -0.315 | 2 | -1.92 | -2 | 74 | 4.66 | 0 |
| SRI-22819 | 0.243 | 1 | -0.143 | 0 | 1664 | 3.15 | 0 |
| SRI-22816 | 0.553 | 1 | 0.393 | 1 | 3768 | 4.11 | 0 |
| SRI-22778 | -0.757 | 3 | -0.13 | 0 | 1331.048 | 2.019 | 0 |

FIGURE 21

TREATMENT OF NEURODEGENERATIVE DISEASES, CAUSATION OF MEMORY ENHANCEMENT, AND ASSAY FOR SCREENING COMPOUNDS FOR SUCH

CROSS-REFERENCE TO RELATED APPLICATIONS

This Application is a National Stage of International Application No. PCT/US2010/052624, filed on Oct. 14, 2010, and claims priority of U.S. Provisional Patent Application No. 61/251,874, filed on Oct. 15, 2009. The disclosures of the prior applications are incorporated herein in their entirety by reference.

FEDERALLY SPONSORED RESEARCH AND DEVELOPMENT

This invention was partially supported by Grant MLSCN: 1U54-HG-003917 and -N01NS-22348 and 1R03MH082367-01 to M.G. from National Institute of Health and the US Government has certain rights in the invention.

TECHNICAL FIELD

The present disclosure relates to a method for treating a patient suffering from a neurodegenerative disease such as Alzheimer's, Parkinson's, and Lou Gehrig's (ALS) disease, and patients with or patients predisposed to developing a learning and memory impairment and/or neurodegeneration not classifiable in any of the above mentioned examples and enhancing memory performance in normal and pathological states, which comprises administering to the patient an effective amount of certain heterocyclic and aromatic compounds. The applications of this disclosure also include all of the situations in which strengthening NF-kB signaling can result in amelioration of patient conditions and is not limited to the central nervous system or the above mentioned central nervous system conditions. A number of the compounds to be employed are novel. The present disclosure also relates to a neuronal human cell-based assay that will assess NF-kB gene up-regulation using a luciferase reporter for screening for compounds for use in treating neurodegenerative diseases as described above.

BACKGROUND ART

Effective treatment for neurodegenerative diseases, such as (without limitation) Alzheimer's, Parkinson's, and Lou Gehrig's disease is still lacking. For example, it has been recently reported that Alzheimer's disease is the seventh leading cause of death in the United States. It has also been reported that 26 million people worldwide, including 5 million Americans, have Alzheimer's disease. Only marginal symptomatologic treatment is available to date. Statistics and projections indicate that 1 in 2 subjects above the age of 80 experience some level of clinically relevant cognitive impairment and with the projections indicating an increase of the average lifespan of the humans the burden deriving to society will be immense.

There are several indications that the NF-kB pathway plays a role in neuronal resilience and in the changes induced by cellular learning such as long term potentiation and depression. Several reports have shown that knocking out NF-kB activity in the brain causes sensitization to toxic stimuli, such as β-amyloid, excitatory aminoacids and to trauma. Also NF-kB activation has been involved in long term potentiation and depression the cellular correlates of learning and memory. In addition, activation of NF-kB is a known anti-apoptosis mechanism. Failure of NF-kB in other systems can also be counteracted by compounds of this disclosure and therefore will be covered by this disclosure.

SUMMARY OF DISCLOSURE

The present disclosure relates to a method for protecting neurons and enhancing memory performance in a patient or for treating a patient suffering from a neurodengenerative disease a memory impairment, or a learning impairment by administering to the patient at least one compound represented by the structures:

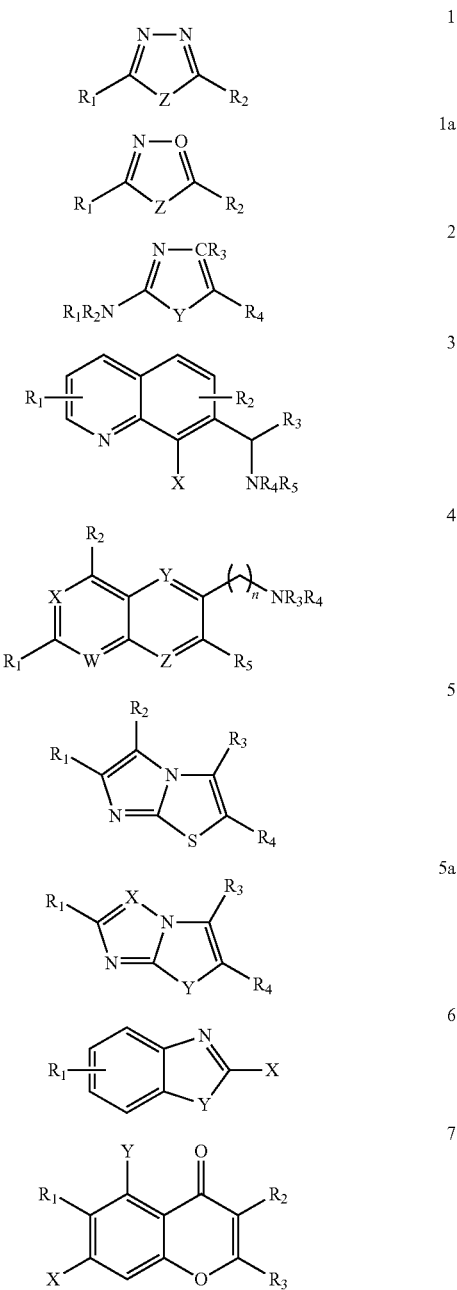

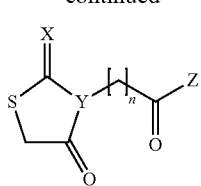

8

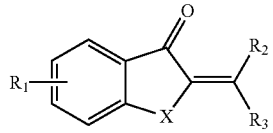

9

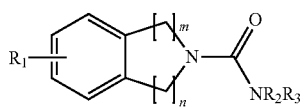

10

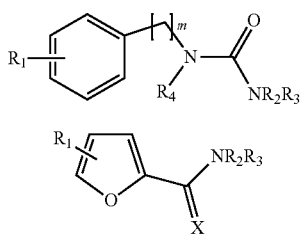

10a

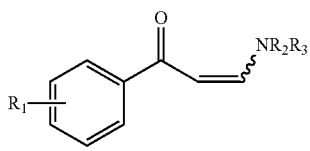

11

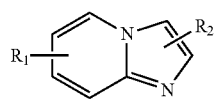

12

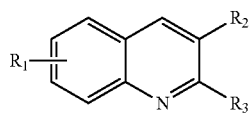

13

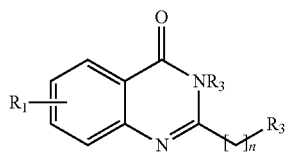

14

15

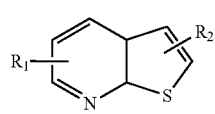

16 a pharmaceutically acceptable salt thereof, a solvate thereof, a prodrug thereof and mixtures thereof; in an amount effective for treating said patient.

In Structure 1, Z represents O, NH, N—$R_3$, S, CH, or $CR_3$; and each $R_1$, $R_2$ and $R_3$ is individually selected from the group consisting of substituted or unsubstituted alkyl, aryl, aralkyl and heteroaryl.

In Structure 1a, Z represents N, CH, or $CR_3$ and each $R_1$, $R_2$ and $R_3$ is individually selected from the group consisting of substituted or unsubstituted alkyl, aryl, aralkyl and heteroaryl.

In Structure 2, Y is O or S; $R_1$ is H, acyl, substituted or unsubstituted alkyl, aryl, aralkyl and heteroaryl; each $R_2$ and $R_4$ is individually selected from the group consisting of substituted or unsubstituted alkyl, aryl, aralkyl and heteroaryl and $R_3$ is selected from the group consisting of H or substituted or unsubstituted alkyl, aryl, aralkyl and heteroaryl.

In Structure 3, X represents $OR_6$ or $NR_6R_7$; each $R_1$ and $R_2$ is individually selected from the group consisting of single or multiple substitutions of H or substituted or unsubstituted alkyl, aryl, aralkyl heteroaryl or acyl, halogen, hydroxy, alkoxy, amino or substituted amino; each $R_3$, $R_4$ and $R_6$ is individually selected from the group consisting of H, substituted or unsubstituted alkyl, aryl, aralkyl and heteroaryl; and each $R_5$ and $R_7$ is individually selected from the group consisting of H, acyl, substituted or unsubstituted alkyl, aryl, aralkyl and heteroaryl.

In Structure 4, each W, X, Y, Z is N or $CR_6$; each $R_1$, $R_2$, $R_4$, $R_5$ and $R_6$ is individually selected from the group consisting of H, substituted or unsubstituted alkyl, aryl, aralkyl and heteroaryl; $R_3$ is H, acyl, substituted or unsubstituted alkyl, aryl, aralkyl and heteroaryl.

In Structure 5, each $R_1$, $R_2$, $R_3$ and $R_4$ is individually selected from the group consisting of H, substituted or unsubstituted alkyl, aryl, aralkyl and heteroaryl.

In Structure 5a, X represents N or $CR_2$; Y represents S or $CR_5R_6$; and each $R_1$, $R_2$, $R_3$, $R_4$, $R_5$ and $R_6$ is individually selected from the group consisting of H, substituted or unsubstituted alkyl, aryl, aralkyl and heteroaryl.

In Structure 6, X represents $R_2$ or $NR_3R_4$; Y represents O, S or $NR_5$; $R_1$ is selected from the group consisting of single or multiple substitutions of H or substituted or unsubstituted alkyl, aryl, aralkyl heteroaryl or acyl, halogen, hydroxy, alkoxy, amino or substituted amino; each $R_2$, $R_3$, and $R_5$ is individually selected from the group consisting of H, substituted or unsubstituted alkyl, aryl, aralkyl and heteroaryl; and $R_4$ is H, acyl, substituted or unsubstituted alkyl, aryl, aralkyl and heteroaryl.

In Structure 7, X represents O—$R_4$ or $NR_4R_5$; each $R_1$, $R_2$, $R_3$, and $R_4$ is individually selected from the group consisting of H, substituted or unsubstituted alkyl, aryl, aralkyl and heteroaryl; and $R_5$ is H, acyl, substituted or unsubstituted alkyl, aryl, aralkyl and heteroaryl.

In Structure 8, X represents O or S; Y represents N or $CR_3$; Z represents $NR_4R_5$ or $CR_4R_5R_6$; each $R_3$, $R_4$, and $R_6$ is individually selected from the group consisting of H, substituted or unsubstituted alkyl, aryl, aralkyl and heteroaryl; and n is 0, 1, 2, 3, or 4.

In Structure 9, X represents O, S or $NR_4$; $R_1$ is selected from the group consisting of single or multiple substitutions of H or substituted or unsubstituted alkyl, aryl, aralkyl heteroaryl or acyl, halogen, hydroxy, alkoxy, amino or substituted amino; and each $R_2$, $R_3$, and $R_4$ is individually selected from the group consisting of H, substituted or unsubstituted alkyl, aryl, aralkyl and heteroaryl.

In Structure 10, $R_1$ is selected from the group consisting of single or multiple substitutions of H or substituted or unsubstituted alkyl, aryl, aralkyl heteroaryl or acyl, halogen, hydroxy, alkoxy, amino or substituted amino; $R_2$ is selected from the group consisting of H, substituted or unsubstituted alkyl, aryl, aralkyl and heteroaryl; $R_3$ is H, acyl, substituted or unsubstituted alkyl, aryl, aralkyl and heteroaryl; m is 0, 1, 2, or 3; and n is 1, 2, or 3.

In Structure 10a, $R_1$ is selected from the group consisting of single or multiple substitutions of H or substituted or unsubstituted alkyl, aryl, aralkyl heteroaryl or acyl, halogen, hydroxy, alkoxy, amino or substituted amino; $R_4$ is selected from the group consisting of H, substituted or unsubstituted alkyl, aryl, aralkyl and heteroaryl; $R_3$ is H, acyl, substituted or unsubstituted alkyl, aryl, aralkyl and heteroaryl; and m is 0, 1, 2, or 3.

In Structures 11 and 12 $R_1$, is selected from the group consisting of single or multiple substitutions of H or substituted or unsubstituted alkyl, aryl, aralkyl heteroaryl or acyl, halogen, hydroxy, alkoxy, amino or substituted amino; $R_2$ is selected from the group consisting of H, substituted or unsubstituted alkyl, aryl, aralkyl and heteroaryl; and $R_3$ is H, acyl, substituted or unsubstituted alkyl, aryl, aralkyl and heteroaryl.

In Structure 13, each $R_1$ and $R_2$ is individually selected from the group consisting of single or multiple substitutions of H or substituted or unsubstituted alkyl, aryl, aralkyl heteroaryl or acyl, halogen, hydroxy, alkoxy, amino or substituted amino.

In Structure 14, $R_1$ is selected from the group consisting of single or multiple substitutions of H or substituted or unsubstituted alkyl, aryl, aralkyl heteroaryl or acyl, halogen, hydroxy, alkoxy, amino or substituted amino; and each $R_2$ and $R_3$ is individually selected from the group consisting of H or substituted or unsubstituted alkyl, aryl, aralkyl heteroaryl or acyl, halogen, hydroxy, alkoxy, amino, substituted amino, alkylthio, cyano or azido.

In Structure 15, $R_1$ is selected from the group consisting of single or multiple substitutions of H or substituted or unsubstituted alkyl, aryl, aralkyl heteroaryl or acyl, halogen, hydroxy, alkoxy, amino or substituted amino, cyano or alkylthio; and each $R_2$ and $R_3$ is individually selected from the group consisting of H or substituted or unsubstituted alkyl, aryl, aralkyl heteroaryl or acyl, halogen, hydroxy, alkoxy, amino, substituted amino, cyano or alkylthio.

In Structure 16, each $R_1$ and $R_2$ is individually selected from the group consisting of single or multiple substitutions of H or substituted or unsubstituted alkyl, aryl, aralkyl heteroaryl or acyl, halogen, hydroxy, alkoxy, amino or substituted amino, cyano, azido or alkylthio.

The present disclosure also relates to treating a patient that is predisposed to developing a neurodegenerative disease, a memory impairment, or a learning impairment. In another embodiment, the method is for improving learning. In yet another embodiment, the method is for preventing or minimizing the decline of memory or improving or maintaining baseline memory.

The present disclosure also relates to novel compounds employed according to this disclosure.

The present disclosure also relates to a neuronal human cell-based assay that will assess NF-kB up-regulation using a luciferase reporter for screening for compounds that can be used in treating neurodegenerative diseases.

Still other objects and advantages of the present disclosure will become readily apparent by those skilled in the art from the following detailed description, wherein it is shown and described preferred embodiments, simply by way of illustration of the best mode contemplated. As will be realized the disclosure is capable of other and different embodiments, and its several details are capable of modifications in various obvious respects, without departing from the disclosure. Accordingly, the description is to be regarded as illustrative in nature and not as restrictive.

SUMMARY OF DRAWINGS

FIG. 12 correlates structures from FIG. 11 with internal SRI designations.

FIG. 21 shows the in silico predicted parameters for the brain distribution of 7 neuron selective compounds. ADMET BBB is the log of brain to blood partition coefficient calculated using the software Pipeline Plot. ADMET BBB Level indicates the ranking of ADMET BBB (0 being very high predicted passive distribution in the brain decreasing down to 3. 4 indicated unpredictable behavior). QPLog Predicted brain/blood partition coefficient (Range=−3.0 to 1.2 higher the better) using the software Quik Prop. CNS: Predicted central nervous system activity on a −2 (inactive) to +2 (active) scale. QPPMDCK: Predicted apparent MDCK cell permeability in nm/sec (v<25 poor; v>500 good). QPlogPo/w: Predicted octanol/water partition coefficient (Range=−2.0 to 6, optimal v>1 and V<4). QPlogPo/w<5 (Lipophilicity); donor HB<=5 (Hydrogen bond donors); acceptHB<=10 (Hydrogen) Rule Of Five: Number of violations of Lipinski's rule of five (Desired values should be: MW<500 (Molecular Weight); bond acceptors.

BEST AND VARIOUS MODES

Figure 1:
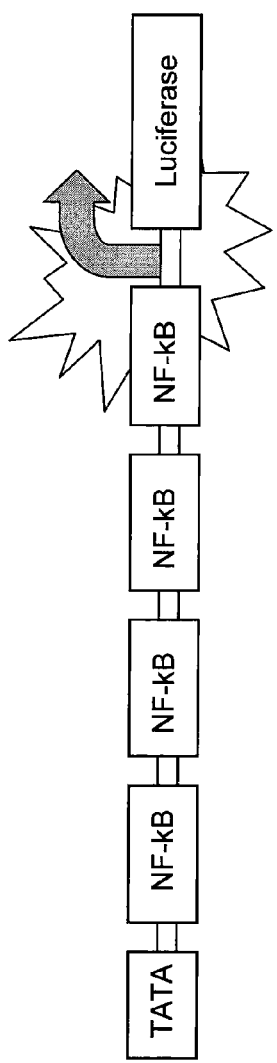
FIG. 1 is a schematic of the construct used in this disclosure. A TATA box has been attached to 4 copies of the NF-kB promoter enhancer sequence to drive firefly luciferase gene transcription.

In particular, the present disclosure relates to use of compounds represented by the following structures:

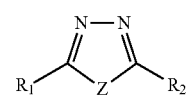

1

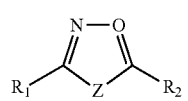

1a

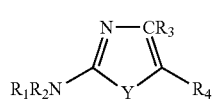

2

-continued

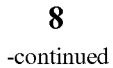

3

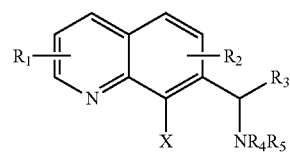

4

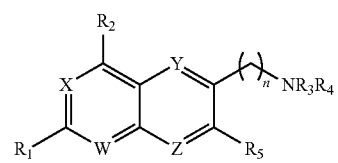

5

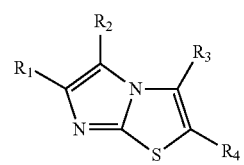

5a

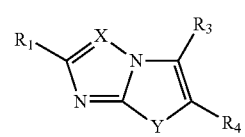

6

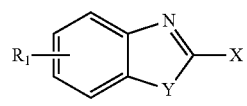

7

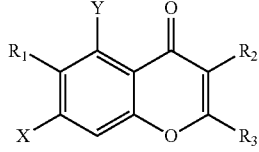

8

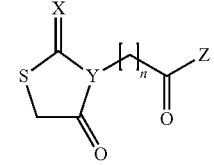

9

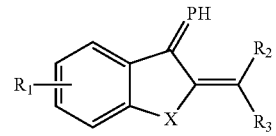

10

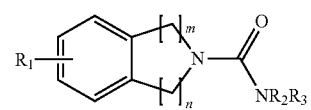

10a

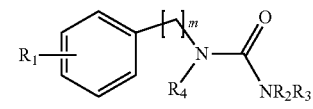

11

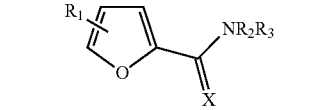

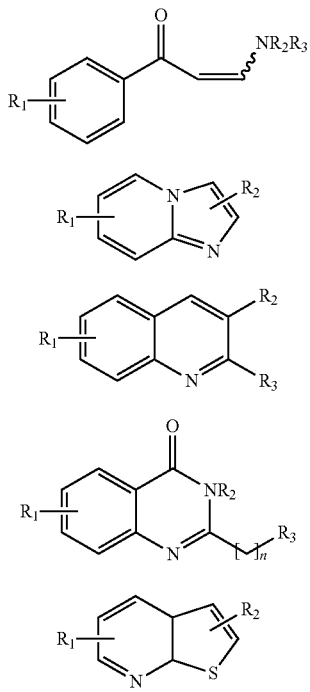

a pharmaceutically acceptable salt thereof, a solvate thereof, a prodrug thereof and mixtures thereof.

In Structure 1, Z represents O, NH, N—$R_3$, S, CH, or $CR_3$; and each $R_1$, $R_2$ and $R_3$ is individually selected from the group consisting of substituted or unsubstituted alkyl, aryl, aralkyl and heteroaryl.

In Structure 1a, Z represents N, CH, or $CR_3$ and each $R_1$, $R_2$ and $R_3$ is individually selected from the group consisting of substituted or unsubstituted alkyl, aryl, aralkyl and heteroaryl.

In Structure 2, Y is O or S; $R_1$ is H, acyl, substituted or unsubstituted alkyl, aryl, aralkyl and heteroaryl; each $R_2$ and $R_4$ is individually selected from the group consisting of substituted or unsubstituted alkyl, aryl, aralkyl and heteroaryl and $R_3$ is selected from the group consisting of H or substituted or unsubstituted alkyl, aryl, aralkyl and heteroaryl.

In Structure 3, X represents $OR_6$ or $NR_6R_7$; each $R_1$ and $R_2$ is individually selected from the group consisting of single or multiple substitutions of H or substituted or unsubstituted alkyl, aryl, aralkyl heteroaryl or acyl, halogen, hydroxy, alkoxy, amino or substituted amino; each $R_3$, $R_4$ and $R_6$ is individually selected from the group consisting of H, substituted or unsubstituted alkyl, aryl, aralkyl and heteroaryl; and each $R_5$ and $R_7$ is individually selected from the group consisting of H, acyl, substituted or unsubstituted alkyl, aryl, aralkyl and heteroaryl.

In Structure 4, each W, X, Y, Z is N or $CR_6$; each $R_1$, $R_2$, $R_4$, $R_5$ and $R_6$ is individually selected from the group consisting of H, substituted or unsubstituted alkyl, aryl, aralkyl and heteroaryl; $R_3$ is H, acyl, substituted or unsubstituted alkyl, aryl, aralkyl and heteroaryl.

In Structure 5, each $R_1$, $R_2$, $R_3$ and $R_4$ is individually selected from the group consisting of H, substituted or unsubstituted alkyl, aryl, aralkyl and heteroaryl.

In Structure 5a, X represents N or $CR_2$; Y represents S or $CR_5R_6$; and each $R_1$, $R_2$, $R_3$, $R_4$, $R_5$ and $R_6$ is individually selected from the group consisting of H, substituted or unsubstituted alkyl, aryl, aralkyl and heteroaryl.

In Structure 6, X represents $R_2$ or $NR_3R_4$; Y represents O, S or $NR_5$; $R_1$ is selected from the group consisting of single or multiple substitutions of H or substituted or unsubstituted alkyl, aryl, aralkyl heteroaryl or acyl, halogen, hydroxy, alkoxy, amino or substituted amino; each $R_2$, $R_3$, and $R_5$ is individually selected from the group consisting of H, substituted or unsubstituted alkyl, aryl, aralkyl and heteroaryl; and $R_4$ is H, acyl, substituted or unsubstituted alkyl, aryl, aralkyl and heteroaryl.

In Structure 7, X represents O—$R_4$ or $NR_4R_5$; each $R_1$, $R_2$, $R_3$, and $R_4$ is individually selected from the group consisting of H, substituted or unsubstituted alkyl, aryl, aralkyl and heteroaryl; and $R_5$ is H, acyl, substituted or unsubstituted alkyl, aryl, aralkyl and heteroaryl.

In Structure 8, X represents O or S; Y represents N or $CR_3$; Z represents $NR_4R_5$ or $CR_4R_5R_6$; each $R_3$, $R_4$, and $R_6$ is individually selected from the group consisting of H, substituted or unsubstituted alkyl, aryl, aralkyl and heteroaryl; and n is 0, 1, 2, 3, or 4.

In Structure 9, X represents O, S or $NR_4$; $R_1$ is selected from the group consisting of single or multiple substitutions of H or substituted or unsubstituted alkyl, aryl, aralkyl heteroaryl or acyl, halogen, hydroxy, alkoxy, amino or substituted amino; and each $R_2$, $R_3$, and $R_4$ is individually selected from the group consisting of H, substituted or unsubstituted alkyl, aryl, aralkyl and heteroaryl.

In Structure 10, $R_1$ is selected from the group consisting of single or multiple substitutions of H or substituted or unsubstituted alkyl, aryl, aralkyl heteroaryl or acyl, halogen, hydroxy, alkoxy, amino or substituted amino; $R_2$ is selected from the group consisting of H, substituted or unsubstituted alkyl, aryl, aralkyl and heteroaryl; $R_3$ is H, acyl, substituted or unsubstituted alkyl, aryl, aralkyl and heteroaryl; m is 0, 1, 2, or 3; and n is 1, 2, or 3.

In Structure 10a, $R_1$, is selected from the group consisting of single or multiple substitutions of H or substituted or unsubstituted alkyl, aryl, aralkyl heteroaryl or acyl, halogen, hydroxy, alkoxy, amino or substituted amino; $R_4$ is selected from the group consisting of H, substituted or unsubstituted alkyl, aryl, aralkyl and heteroaryl; $R_3$ is H, acyl, substituted or unsubstituted alkyl, aryl, aralkyl and heteroaryl; and m is 0, 1, 2, or 3.

In Structures 11 and 12, $R_1$ is selected from the group consisting of single or multiple substitutions of H or substituted or unsubstituted alkyl, aryl, aralkyl heteroaryl or acyl, halogen, hydroxy, alkoxy, amino or substituted amino; $R_2$ is selected from the group consisting of H, substituted or unsubstituted alkyl, aryl, aralkyl and heteroaryl; and $R_3$ is H, acyl, substituted or unsubstituted alkyl, aryl, aralkyl and heteroaryl.

In Structure 13, each $R_1$ and $R_2$ is individually selected from the group consisting of single or multiple substitutions of H or substituted or unsubstituted alkyl, aryl, aralkyl heteroaryl or acyl, halogen, hydroxy, alkoxy, amino or substituted amino.

In Structure 14, $R_1$ is selected from the group consisting of single or multiple substitutions of H or substituted or unsubstituted alkyl, aryl, aralkyl heteroaryl or acyl, halogen, hydroxy, alkoxy, amino or substituted amino; and each $R_2$ and $R_3$ is individually selected from the group consisting of H or substituted or unsubstituted alkyl, aryl, aralkyl heteroaryl or acyl, halogen, hydroxy, alkoxy, amino, substituted amino, alkylthio, cyano or azido.

In Structure 15, $R_1$ is selected from the group consisting of single or multiple substitutions of H or substituted or unsubstituted alkyl, aryl, aralkyl heteroaryl or acyl, halogen, hydroxy, alkoxy, amino or substituted amino, cyano or alkylthio; and each $R_2$ and $R_3$ is individually selected from the group consisting of H or substituted or unsubstituted alkyl, aryl, aralkyl heteroaryl or acyl, halogen, hydroxy, alkoxy, amino, substituted amino, cyano or alkylthio.

In Structure 16, each $R_1$ and $R_2$ is individually selected from the group consisting of single or multiple substitutions of H or substituted or unsubstituted alkyl, aryl, aralkyl heteroaryl or acyl, halogen, hydroxy, alkoxy, amino or substituted amino, cyano, azido or alkylthio.

Listed below are definitions of various terms used to describe this invention. These definitions apply to the terms as they are used throughout this specification, unless otherwise limited in specific instances, either individually or as part of a larger group.

Typical aliphatic acyl groups contain 1 to 6 carbon atoms and include formyl, acetyl, propionyl and isobutyryl.

Typical aromatic acyl groups include unsubstituted and alkyl substituted aromatic groups containing 7 to 10 carbon atoms in the aromatic ring. When substituted the alkyl group typically contains 1-6 carbon atoms. Typical aromatic acyl groups include benzoyl para-toluoyl and phenylacetyl.

The term "alkyl" refers to saturated or unsaturated (alkenyl or alkynyl) straight, branched chain, or cyclic, unsubstituted hydrocarbon groups of typically 1 to 22 carbon atoms, more typically 1 to 8 carbon atoms, and even more typically 1 to 4 carbon atoms.

Examples of suitable alkyl groups include methyl, ethyl and propyl. Examples of branched alkyl groups include isopropyl and t-butyl. Examples of cyclic alkyl groups include cyclohexyl and cyclopropylmethyl. Examples of unsaturated alkyl groups include ethynyl, cyclopentenyl, and allyl. Examples of substituted alkyl groups include 2-methoxyethyl, 2,2,2-trifluoroethyl, and 2-diethylaminocyclopentenyl. Suitable monoalkylamino groups for X contain 1-6 carbon atoms and include monomethylamino, monoethylamino, mono-isopropylamino, mono-n-propylamino, mono-isobutyl-amino, mono-n-butylamino, mono-n-hexylamino, monophenethylamino, or mono-2-pyridylamino. The alkyl moiety can be straight, branched, or cyclic chain.

Suitable dialkylamino groups typically contain 1-6 carbon atoms in each alkyl group. The alkyl groups can be the same or different and can be straight, branched or cyclic chain. Examples of some suitable groups are dimethylamino, diethylamino, ethylmethylamino, dipropylamino, dibutylamino, dipentylamino, dihexylamino, methylpentylamino, ethylpropylamino and ethylhexylamino.

Examples of halo groups are Cl, F, Br and I.

The term "aryl" refers to monocyclic or polycyclic aromatic hydrocarbon groups having 6 to 14 carbon atoms in the ring portion, such as phenyl, naphthyl, biphenyl, and diphenyl groups, each of which may be substituted such as with a halo or alkyl group.

The term "aralkyl" or "alkylaryl" refers to an aryl group bonded directly through an alkyl group, such as benzyl or phenethyl.

The term "heteroaryl", refers to an optionally substituted, unsaturated aromatic cyclic group, for example, which is a 5 to 7 membered monocyclic, 7 to 11 membered bicyclic, or 10 to 15 membered tricyclic ring system, which has at least one heteroatom and at least one carbon atom in the ring. Each ring of the heterocyclic group containing a heteroatom may have 1, 2 or 3 heteroatoms selected from nitrogen atoms, oxygen atoms and sulfur atoms, where the nitrogen and sulfur heteroatoms may also optionally be oxidized and the nitrogen heteroatoms may also optionally be quaternized. Examples of heteroaryl groups are pyridyl, imidazolyl, oxazolyl, thiazolyl, isothiazolyl, furyl, thienyl and indolyl.

When substituted, the above groups are typically substituted with a halo, alkyl, alkoxy or amino group.

It is of course understood that the compounds of the present disclosure relate to all optical isomers and stereo-isomers at the various possible atoms of the molecule, unless specified otherwise.

The compounds according to this disclosure may form prodrugs at hydroxyl or amino functionalities using alkoxy, amino acids, etc. groups as the prodrug forming moieties. For instance, the hydroxymethyl position may form mono-, di- or triphosphates and again these phosphates can form prodrugs. For example, see Meier, CycloSal Phosphates as Chemical Trojan Horses for Intracellular Nucleotide Glycosyl-Monophosphate Delivery—Chemistry Meets Biology, European Journal of Organic Chemistry (2006), (5), 1081-1102, Wiley-VCH Verlag GmbH & Co. KGaA, Chemical Abstracts 144: 391234; Drontle et al, Designing a Pronucleotide Stratagem: Lessons from Amino Acid Phosphoramidates of Anticancer and Antiviral Pyrimidines, Mini-Reviews in Medicinal Chemistry (2004), 4(4), 409-419, Bentham Science Publishers Ltd., Chemical Abstracts 141:230392; Cahard et al, Aryloxy Phosphoramidate Triesters as Protides, Mini-Reviews in Medicinal Chemistry (2004), 4(4), 371-381, Bentham Science Publishers Ltd., Chemical Abstracts, 141:218130 and Meier, CycloSal-Pronucleotides-Design of the Concept, Chemistry, and Antiviral activity, Advances in Antiviral Drug Design (2004), 4, 147-213, Elsevier B. V, Chemical Abstracts 141:133365.

Preparations of such prodrug derivatives are discussed in various literature sources (examples are: Alexander et al., J. Med. Chem. 1988, 31, 318; Aligas-Martin et al., PCT WO pp/41531, p. 30). The nitrogen function converted in preparing these derivatives is one (or more) of the nitrogen atoms of a compound of the disclosure.

"Pharmaceutically acceptable salts" refer to derivatives of the disclosed compounds wherein the parent compound is modified by making acid or base salts thereof. The compounds of this disclosure form acid and base addition salts with a wide variety of organic and inorganic acids and bases and includes the physiologically acceptable salts which are often used in pharmaceutical chemistry. Such salts are also part of this disclosure. Typical inorganic acids used to form such salts include hydrochloric, hydrobromic, hydroiodic, nitric, sulfuric, phosphoric, hypophosphoric and the like. Salts derived from organic acids, such as aliphatic mono and dicarboxylic acids, phenyl substituted alkonic acids, hydroxyalkanoic and hydroxyalkandioic acids, aromatic acids, aliphatic and aromatic sulfonic acids, may also be used. Such pharmaceutically acceptable salts thus include acetate, phenylacetate, trifluoroacetate, acrylate, ascorbate, benzoate, chlorobenzoate, dinitrobenzoate, hydroxybenzoate, methoxybenzoate, methylbenzoate, o-acetoxybenzoate, naphthalene-2-benzoate, bromide, isobutyrate, phenylbutyrate, β-hydroxybutyrate, butyne-1,4-dioate, hexyne-1,4-dioate, cabrate, caprylate, chloride, cinnamate, citrate, formate, fumarate, glycollate, heptanoate, hippurate, lactate, malate, maleate, hydroxymaleate, malonate, mandelate, mesylate, nicotinate, isonicotinate, nitrate, oxalate, phthalate, teraphthalate, phosphate, monohydrogenphosphate, dihydrogenphosphate, metaphosphate, pyrophosphate, propiolate, propionate, phenylpropionate, salicylate, sebacate, succinate, suberate, sulfate, bisulfate, pyrosulfate, sulfite, bisulfite, sulfonate, benzene-sulfonate, p-bromobenzenesulfonate, chlorobenzenesulfonate, ethanesulfonate, 2-hydroxyethanesulfonate, methanesulfonate, naphthalene-1-sulfonate, naphthalene-2-sulfonate, p-toleunesulfonate, xylenesulfonate, tartarate, and the like.

Bases commonly used for formation of salts include ammonium hydroxide and alkali and alkaline earth metal hydroxides, carbonates, as well as aliphatic and primary, secondary and tertiary amines, aliphatic diamines. Bases especially useful in the preparation of addition salts include sodium hydroxide, potassium hydroxide, ammonium hydroxide, potassium carbonate, methylamine, diethylamine, and ethylene diamine.

"Solvates" refers to the compound formed by the interaction of a solvent and a solute and includes hydrates. Solvates are usually crystalline solid adducts containing solvent molecules within the crystal structure, in either stoichiometric or nonstoichiometric proportions.

Many of the compounds employed according to the present disclosure are available commercially. Those compounds to be employed in the present disclosure that are novel can be made by those of ordinary skill in the art once aware of the present disclosure without undue experimentation by methods available in the art.

For instance with respect to compounds of Structure 1, see Yale et al., 3,5-Disubstituted-1,2,4-oxadiazoles and 4,5-dihydro-3,5-disubstituted-1,2,4-oxadiazoles; Journal of Heterocyclic Chemistry (1978), 15(8), 1373-8.

With respect to compounds of Structure 2, see Mane et al, Synthesis of 2-aryl-3-[p-(2'-substituted-aminothiazol-4'-yl)phenyl]-4-thiazolidinones, Indian Journal of Chemistry, Section B: Organic Chemistry Including Medicinal Chemistry (1983), 22B(1), 81-2; Pathak et al., Synthesis of some fluoroarylthiazoles and related compounds as potential fungicides, Bokin Bobai (1981), 9(10), 477-80 and Maziere et al., Fluoroaryl derivatives of some heterocyclic compounds, Bulletin de la Societe Chimique de France (1963) 1000-3.

With respect to compounds of Structure 3, see Hekimi, WO 2008/014602 entitled Preparation of quinoline derivatives as active CLK-1 inhibitors. With respect to compounds of Structure 4, see Bowman et al., Protein Flexibility and Species Specificity in Structure-Based Drug Discovery: Dihydrofolate Reductase as a Test System, Journal of the American Chemical Society (2007), 129(12), 3634-3640; Sutherland et al., Three-dimensional quantitative structure-activity and structure-selectivity relationships of dihydrofolate reductase inhibitors, Journal of Computer-Aided Molecular Design (2004), 18(5), 309-331, Kluwer Academic Publishers; Debnath, Pharmacophore Mapping of a Series of 2,4-Diamino-5-deazapteridine Inhibitors of *Mycobacterium avium* Complex Dihydrofolate Reductase, Journal of Medicinal Chemistry (2002), 45(1), 41-53, American Chemical Society; Suling et al., Antimycobacterial activities of 2,4-diamino-5-deazapteridine derivatives and effects on mycobacterial dihydrofolate reductase, Antimicrobial Agents and Chemotherapy (2000), 44(10), 2784-2793, American Society for Microbiology; Piper et al., Lipophilic antifolates as agents against opportunistic infections. 1. Agents superior to trimetrexate and piritrexim against *Toxoplasma gondii* and *Pneumocystis carinii* in in vitro evaluations, Journal of Medicinal Chemistry (1996), 39(6), 1271-80, American Chemical Society.

With respect to compounds of Structure 5, see Ashwell et al. WO 2006/044869 entitled Preparation of pyrimidinyl imidazooxazoles and imidazothiazoles as inhibitors of p38 MAP kinase; Aggarwal et al., Hypervalent iodine in the synthesis of bridgehead heterocycles. A facile route to the synthesis of 6-arylimidazo[2,1-b]thiazoles using [hydroxy(tosyloxy)iodo]benzene, Synthetic Communications (2006), 36(7), 875-879; Ashwell et al., WO 2004110990 entitled Preparation of pyrimidinyl imidazothiazoles and imidazooxazoles as inhibitors of p38; O'Daly et al., Electrophilic substitution of imidazo[2,1-b]thiazoles, Journal of the Chemical Society, Perkin Transactions 1: Organic and Bio-Organic Chemistry (1972-1999) (1991), (4), 855-60; Meakins et al., Substituted imidazo[2,1-b]thiazoles from 2-aminothiazoles and α-bromo ketones: efficient preparation and proof of structure, Journal of the Chemical Society, Perkin Transactions 1: Organic and Bio-Organic Chemistry (1972-1999) (1989), (3), 643-8; Hoffmann et al., Tetramethoxyethylene. III; Chemische Berichte (1966), 99(6), 1899-1905; and Buu-Hoi, Reaction of ω-bromoacetophenones with 2-aminothiazole and 2-aminobenzothiazoles, Bulletin de la Societe Chimique de France (1966), (4), 1277-9.

With respect to compounds of Structure 6, see Wells et al., 4-Substituted 4-Hydroxycyclohexa-2,5-dien-1-ones with Selective Activities against Colon and Renal Cancer Cell Lines, Journal of Medicinal Chemistry (2003), 46(4), 532-541, American Chemical Society; and Stevens et al. WO 2003/004479 entitled Preparation of 4-arylquinols and analogs thereof as antiproliferative agents, anticancer agents, antimycobacterial agents, antituberculosis agents, and/or thioredoxin/thioredoxin reductase inhibitors.

With respect to compounds of Structure 7, see Botting et al., WO 2004/069774 entitled Synthesis of 13C-labeled estrogen analogs; Bondarenko et al., Synthesis of Analogs of Natural Isoflavonoids Containing Phloroglucinol, Chemistry of Natural Compounds (Translation of Khimiya Prirodnykh Soedinenii) (2003), 39(3), 271-275, Kluwer Academic/Consultants Bureau; Liu et al, Journal of Heterocyclic Chemistry (1991), 28(6), 1641-2; and Pivovarenko et al., Synthesis of 5,7-dihydroxyisoflavones and their heterocyclic analogs using acetoformic anhydride, Dopovidi Akademii Nauk Ukrains'koi RSR, Seriya B: Geologichni, Khimichni to Biologichni Nauki (1985), (7), 44-7.

With respect to compounds of Structure 8, see Gorishnii et al., Synthesis and properties of rhodanine carboxamides, Farmatsevtichnii Zhurnal (Kiev) (2001), (2), 64-67; and Gorishnyi et al., Synthesis and antiphlogistic activity of 5-aryliden-erhodanin-3-alkanoic acid amides, Farmatsevtichnii Zhurnal (Kiev) (1995), (4), 50-53.

With respect to compounds of Structure 9, see Vettel et al., DE 10039748 entitled Production of 3-oxobenzo[b]thiophene methine dyes; Kucharczyk et al., Sodium borohydride reduction of 2,3-dihydrothianaphthen-3-ones, Collection of Czechoslovak Chemical Communications (1968), 33(1), 92-9; Treibs, Pyrrole chemistry, Rev. Chim., Acad. Rep. Populaire Roumaine (1962), 7(2), 1345-66, Kucharczyk et al., Improved preparative method for thianaphthene and its 2-substituted derivatives, Chemistry & Industry (London, United Kingdom) (1964), (23), 976; Tsekhanskii, Absorption spectra of the nitrobenzamide derivatives of 4-aminodiphenylmethane and 4-amino-4'-dimethylaminodiphenyl-methane, Izvestiya Vysshikh Uchebnykh Zavedenii, Khimiya i Khimicheskaya Tekhnologiya (1963), 6(2), 252-6; Hallgas, Comparison of measured and calculated lipophilicity of substituted aurones and related compounds, Journal of Chromatography, B: Analytical Technologies in the Biomedical and Life Sciences (2004), 801(2), 229-235, Elsevier B.V.

With respect to compounds of Structure 10, see Hedrich et al., U.S. Pat. No. 4,428,881 entitled Control of unwanted vegetation with N-carbamylindolines; and Tachdjian et al., US 2006045953 entitled Aromatic amides and ureas and their uses as sweet and/or umami flavor modifiers, tastants and taste enhancers. With respect to compounds of Structure 11, see Otten et al., The reaction of α-amino-substituted diphenylphosphine oxide anions with elemental sulfur and selenium. A new route to thio- and selenoamides, Recueil des Travaux Chimiques des Pays-Bas (1994), 113(11), 499-506, Elsevier; Haynes et al., New chemosterilants for boll weevils, U. S., Agric. Res. Serv., South. Reg., [Rep.] (1976), ARS-S-131, 30 pp.; Sullivan et al., U.S. Pat. No. 2,875,202 entited Thiofuramides; and Naylor et al., U.S. Pat. No. 2,723,969 entitled Neoprene vulcanization accelerators.

With respect to compounds of Structure 12, see Fischer, Vinylogous acyl compounds. XIX. Vinylogous acyl group migration in 2-aminophenol. A contribution to the isomerization mechanism of mixed diacyl derivatives of 2-aminophenol, Journal fuer Praktische Chemie (Leipzig) (1980), 322(1), 99-124. With respect to compounds of Structure 13, see Dossetter et al., WO 2002066477 entitled Preparation of substituted imidazopyridines for antagonizing gonadotropin releasing hormone activity; Bravi et al. WO 2007039146 entitled Preparation of 4-carboxypyrazoles as antivirals for treatment of hepatitis C virus (HCV) infection; Godovikova et al., Orientation of bromination reaction of 2-aryl(alkyl) pyrimidazoles, Izvestiya Akademii Nauk SSSR, Seriya Khimicheskaya (1965), (8), 1434-41; and Buu-Hoi et al., Thiophene series. III. Indoles, naphthindoles, pyrrocolines, and pyrimidazoles derived from the thiophene nucleus, Recueil des Travaux Chimiques des Pays-Bas et de la Belgique (1949), 68, 441-72.

With respect to compounds of Structure 15, see Deepthi et al., Microwave induced dry media DDQ oxidation—a one step synthesis of 2-arylquinazolin-4(3H)-ones, Indian Journal of Chemistry, Section B: Organic Chemistry Including Medicinal Chemistry (2000), 39B(3), 220-222; Desai et al., Quinoline and quinazoline compounds as antitubercular agents, Asian Journal of Chemistry (1998), 10(3), 615-617, Asian Journal of Chemistry; Houghten et al. U.S. Pat. No. 5,783,577 entitled Synthesis of quinazolinone combinatorial libraries and derivatives thereof; Houghten et al., WO 97/10221 entitled Synthesis of quinazolinone libraries; Couture et al., An expeditious synthesis of 2-aryl- and 2-alkylquinazolin-4(3H)-ones, Synthesis (1991), (11), 1009-10; Paterson et al., 1,2,3-Benzotriazin-4-ones and related systems. III. Thermal decomposition of 3-arylideneamino-1,2,3-benzotriazin-4-ones. New synthesis of 2-arylquinazolin-4-one; Breuer et al., U.S. Pat. No. 3,753,981 entitled 2-Styryl-4-aminoquinazolines; Matsuoka et al., Fluorescent whitening agents for synthetic fibers. 41. Fluorescence of some quinazolones, Kogyo Kagaku Zasshi (1970), 73(10), 2195-9; Patel et al., Niementowski 4-oxoquinazoline synthesis. I. Modification and mechanism, J. Indian Chem. Soc. (1965), 42(8), 531-5; Mantescu et al. Tritiation of pyrimidines by HTO in the presence of aluminum chloride, J. Labelled Compds. (1965), 1(3), 178-81; Serzhanina et al., Syntheses and transformations of pyrimidine derivatives. XVI. Activity of methyl groups in 2-methylquinazoline derivatives, Zhurnal Organicheskoi Khimii (1965), 1(7), 1303-6; Dhatt et al., 2-Styryl derivatives of 4(3)-quinazolones as potential antimalarials and amebicides, Current Science (1961), 30, 179-80; Mandasescu et al., Reactivity of methyl groups of benzodiazine. II. Condensation of 2-methylbenzodiazines with aldehydes, Acad. Rep. Populare Romine, Filiala Iasi, Studii Cercetari Stiint., Chim. (1960), 11, 75-85; Kilroe Smith, Syntheses in the quinazolone series. VI. Synthesis of 1,2,3,4-tetrahydro-2-aryl-4-oxoquinazolines, Tetrahedron (1957), 1, 38-44; Stephen, Syntheses in the quinazolone series. IV. Conversion of N-aroylorthanilamides to 2-arylquinazol-4-ones, Journal of the Chemical Society (1956) 4420-1; and Bogert, Researches on Quinazolones. XXVI. Synthesis of Some Stilbazoles, Journal of the American Chemical Society (1911), 32, 1654-64. With respect to compounds of Structure 16, see Vieweg et al., Synthesis of new 4-oxo-4H-pyrido[3′,2′:4,5]thieno[3,2-d]-1,3-oxazines, Pharmazie (1990), 45(10), 731-3.

Representative compounds suitable for the treatment according to the present disclosure along with their IC50 values are disclosed in the following Table:

| Structure Class | ID | MOLSTRUCTURE | MW | IC50 |
|---|---|---|---|---|
| 1, 1a | AB00093511 | | 286.7201 | 0.079 |
| | AB00093467 | | 282.3016 | 0.082 |
| | AB00093558 | | 266.3022 | 0.1 |

-continued
| Structure Class | ID | MOLSTRUCTURE | MW | IC50 |
|---|---|---|---|---|
| | AB00084000 | 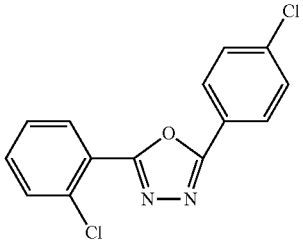 [SMILES: Clc1ccc(-c2nnc(-c3ccccc3Cl)o2)cc1] | 291.1387 | 0.062 |
| | AB00027137 | 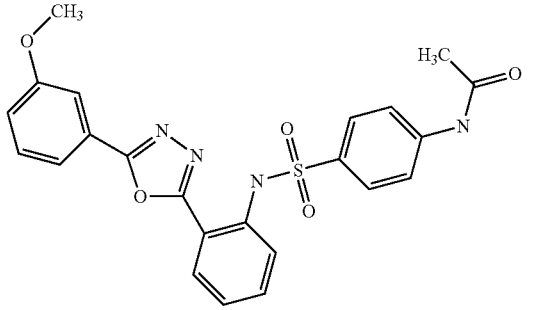 [SMILES: COc1cccc(-c2nnc(-c3ccccc3NS(=O)(=O)c3ccc(NC(C)=O)cc3)o2)c1] | 464.5037 | 0.13 |
| | AB00101507 | 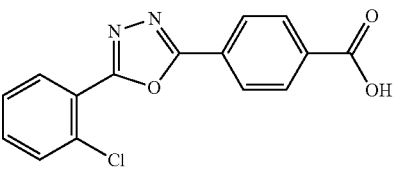 [SMILES: O=C(O)c1ccc(-c2nnc(-c3ccccc3Cl)o2)cc1] | 300.7036 | 0.337 |
| | AB00092734 | 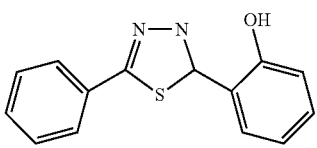 [SMILES: Oc1ccccc1C1NN=C(c2ccccc2)S1] | 256.3285 | 0.382 |
| | AB00093094 | 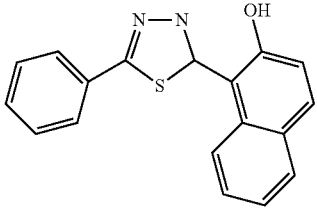 [SMILES: Oc1ccc2ccccc2c1C1NN=C(c2ccccc2)S1] | 306.3891 | 0.788 |
| | AB00093093 | 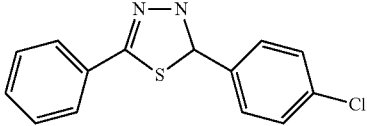 [SMILES: Clc1ccc(C2NN=C(c3ccccc3)S2)cc1] | 274.7742 | 4.062 |
| | AB00101695 | 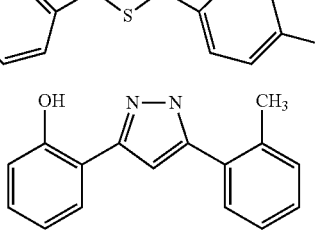 | 250.3028 | 0.579 |

-continued
| Structure Class | ID | MOLSTRUCTURE | MW | IC50 |
|---|---|---|---|---|
| | AB00440877 | 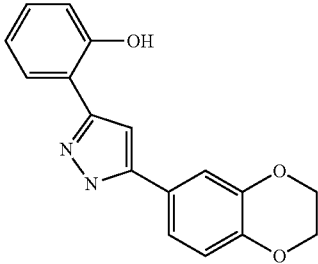 [SMILES: Oc1ccccc1-c1cc(-c2ccc3c(c2)OCCO3)[nH]n1] | 294.3127 | 0.639 |
| | AB00461411 | 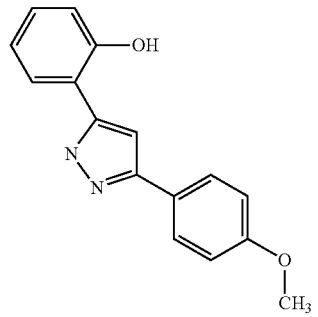 [SMILES: COc1ccc(-c2cc(-c3ccccc3O)[nH]n2)cc1] | 266.3022 | 0.968 |
| 2 | AB00097765 | 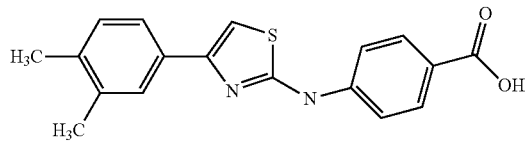 | 324.4044 | 0.062 |
| | | 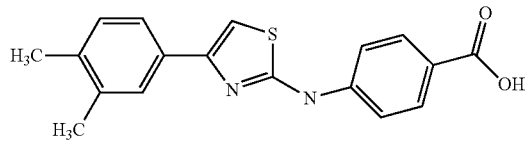 [SMILES: Cc1ccc(-c2csc(Nc3ccc(C(=O)O)cc3)n2)cc1C] | | |
| | AB00079697 | 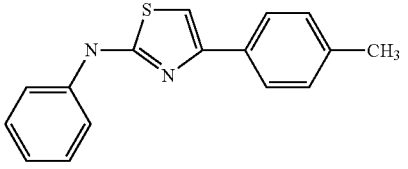 [SMILES: Cc1ccc(-c2csc(Nc3ccccc3)n2)cc1] | 266.3674 | 0.142 |
| | AB00101290 | 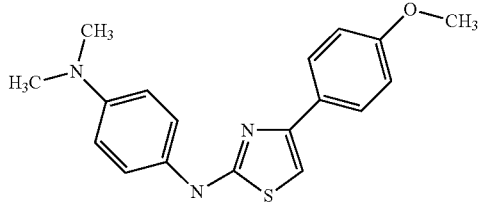 | 325.4356 | 0.144 |
| | AB00097765 | 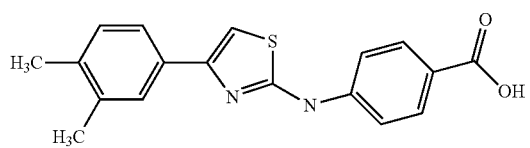 | 324.4044 | 0.062 |

-continued
| Structure Class | ID | MOLSTRUCTURE | MW | IC50 |
|---|---|---|---|---|
| | AB00074195 | 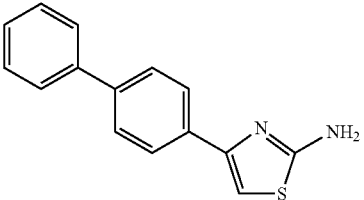 [SMILES: Nc1nc(-c2ccc(-c3ccccc3)cc2)cs1] | 252.3403 | 0.122 |
| | AB00095939 | 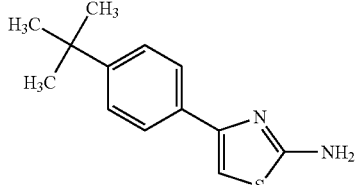 | 232.3499 | 0.133 |
| | AB00546606 | 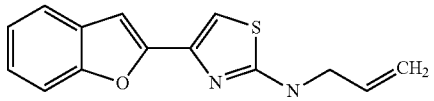 [SMILES: C=CCNc1nc(-c2cc3ccccc3o2)cs1] | 256.3285 | 0.598 |
| | AB00613917 | 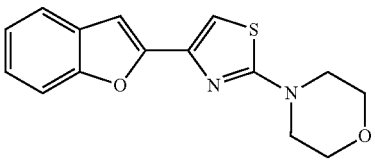 [SMILES: c1ccc2oc(-c3csc(N4CCOCC4)n3)cc2c1] | 286.355 | 0.966 |
| | AB00546194 | 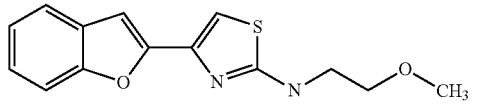 [SMILES: COCCNc1nc(-c2cc3ccccc3o2)cs1] | 274.3439 | 1.396 |
| 3 | AB00101018 | 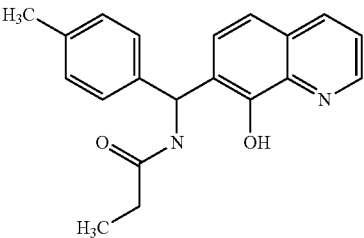 [SMILES: CCC(=O)NC(c1ccc(C)cc1)c1ccc2cccnc2c1O] | 320.3946 | 3.172 |
| | AB00101133 | 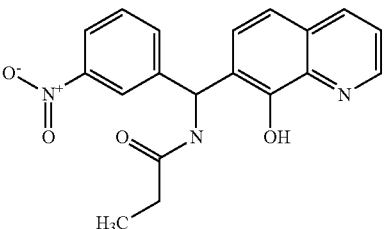 | 351.365 | 3.7 |
| | AB00100961 | 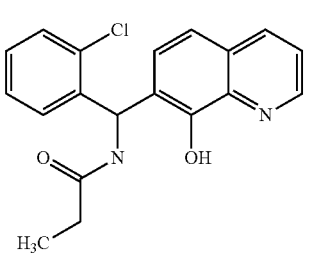 [SMILES: CCC(=O)NC(c1ccccc1Cl)c1ccc2cccnc2c1O] | 340.8125 | 3.967 |

-continued

| Structure Class | ID | MOLSTRUCTURE | MW | IC50 |
|---|---|---|---|---|
| 4 | AB00443206 | | 378.3598 | 0.123 |
| | AB00171904 | | 453.4614 | 0.159 |
| | AB00174102 | | 509.5697 | 0.345 |
| 5, 5a | AB00093745 | | 279.1598 | 0.251 |
| | AB00093742 | | 218.2542 | 0.382 |
| | AB00315863 | | 284.3827 | 0.65 |
| | AB00475708 | | 274.4091 | 1.926 |

-continued

| Structure Class | ID | MOLSTRUCTURE | MW | IC50 |
|---|---|---|---|---|
| | AB00428616 | | 321.8092 | 2.412 |
| | AB00371839 | | 251.2655 | 0.125 |
| | AB00421150 | | 260.382 | 12.577 |
| 6 | AB00011625 | | 432.9262 | 0.111 |
| | AB00012207 | | 452.5985 | 0.155 |
| | AB00003451 | | 464.4885 | 0.156 |

-continued

| Structure Class | ID | MOLSTRUCTURE | MW | IC50 |
|---|---|---|---|---|
|  | AB00547004 |  | 441.5125 | 0.155 |
|  | AB00317535 |  | 398.5305 | 0.328 |
|  | AB00542926 |  | 482.3591 | 0.393 |
| 7 | AB00052939 |  | 298.2981 | 1.725 |
|  | AB00431689 |  | 312.3252 | 4.524 |

| Structure Class | ID | MOLSTRUCTURE | MW | IC50 |
|---|---|---|---|---|
| | AB00390364 | 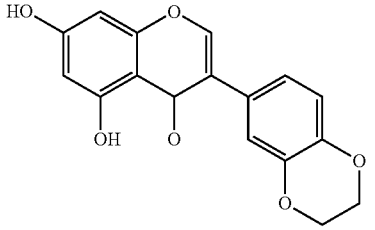 [SMILES: Oc1cc(O)c2c(c1)OC=C(c1ccc3c(c1)OCCO3)C2O] | 312.2816 | 22.698 |
| 8 | AB00121550 | 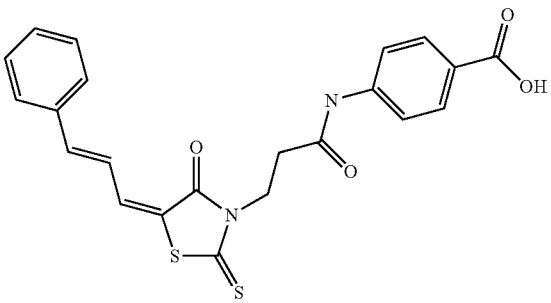 [SMILES: O=C(CCN1C(=O)/C(=C\C=C\c2ccccc2)SC1=S)Nc1ccc(C(=O)O)cc1] | 438.5278 | 0.545 |
| | AB00120582 | 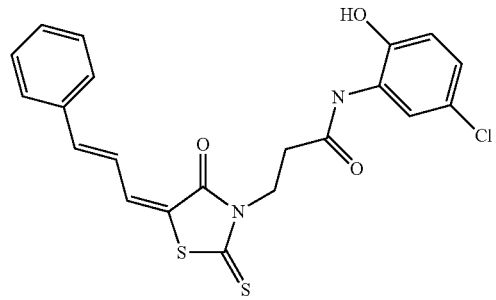 [SMILES: O=C(CCN1C(=O)/C(=C\C=C\c2ccccc2)SC1=S)Nc1cc(Cl)ccc1O] | 444.9622 | 145.666 |
| | AB00089877 | 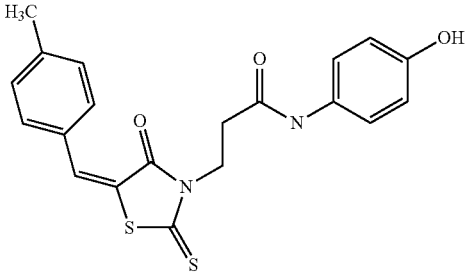 [SMILES: Cc1ccc(/C=C2/SC(=S)N(CCC(=O)Nc3ccc(O)cc3)C2=O)cc1] | 398.5061 | 1312.209 |
| 9 | AB00083765 | 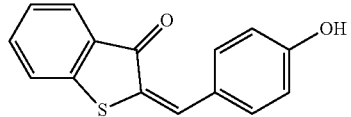 [SMILES: O=C1/C(=C\c2ccc(O)cc2)Sc2ccccc21] | 254.3098 | 3.719 |
| | AB00534272 | 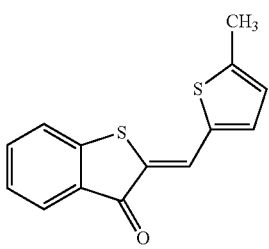 [SMILES: Cc1ccc(/C=C2\Sc3ccccc3C2=O)s1] | 258.3632 | 5.975 |

-continued

| Structure Class | ID | MOLSTRUCTURE | MW | IC50 |
|---|---|---|---|---|
| | AB00083422 | | 228.2715 | 3651.481 |
| 10, 10a | AB00105762 | | 256.2821 | 0.18 |
| | AB00616066 | | 266.3458 | 0.361 |
| | AB00022459 | | 294.4 | 0.065 |
| | AB00013805 | | 338.4536 | 0.067 |

-continued

| Structure Class | ID | MOLSTRUCTURE | MW | IC50 |
|---|---|---|---|---|
| | AB00616088 | | 314.3004 | 0.114 |
| | AB00329861 | | 268.3181 | 0.697 |
| 11 | AB00092070 | | 307.8013 | 0.775 |
| | AB00092117 | | 307.8013 | 3.403 |
| | AB00091724 | | 342.2464 | 5.186 |
| 12 | AB00087011 | | 273.7214 | 0.213 |

-continued
| Structure Class | ID | MOLSTRUCTURE | MW | IC50 |
|---|---|---|---|---|
| | AB00101723 | 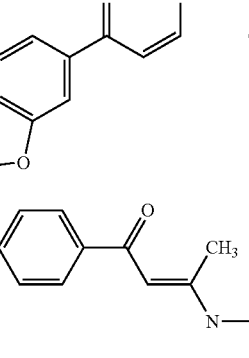 | 317.7313 | 0.213 |
| | AB00102118 | 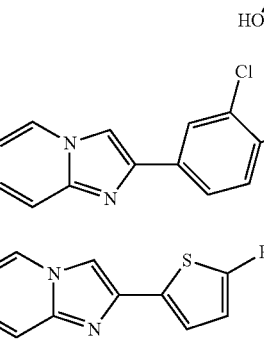 | 283.3299 | 0.235 |
| 13 | AB00548181 | 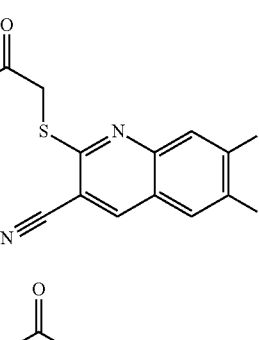 | 342.0241 | 0.062 |
| | AB00528862 | 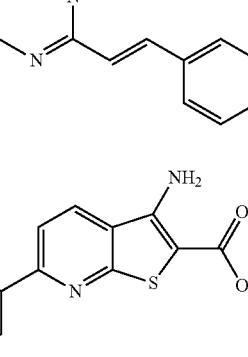 | 279.1598 | 0.094 |
| 14 | AB00614173 | 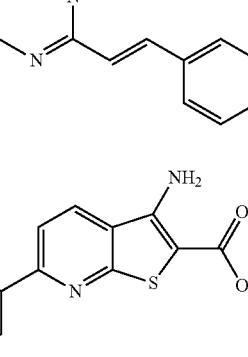 | 300.3385 | 0.104 |
| 15 | AB00097657 | 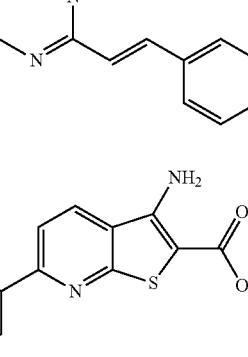 | 264.2862 | 0.064 |
| 16 | AB00079098 | 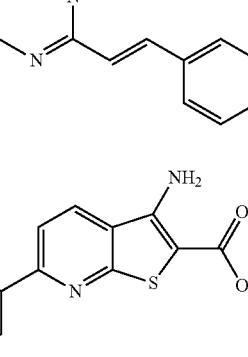 | 284.3391 | 0.067 |

Non-limiting examples of neurodegenerative diseases to be treated according to this disclosure are Alzheimer, Parkinson, Amyotrophic lateral sclerosis, Spinal Muscular Atrophy, Brain traumatic injury and associated neurodegeneration, vascular dementia, Huntington disease and memory and learning deficit (ADHD, mental retardation).

The following is a description of the assay according to the present disclosure.

Figure 2:
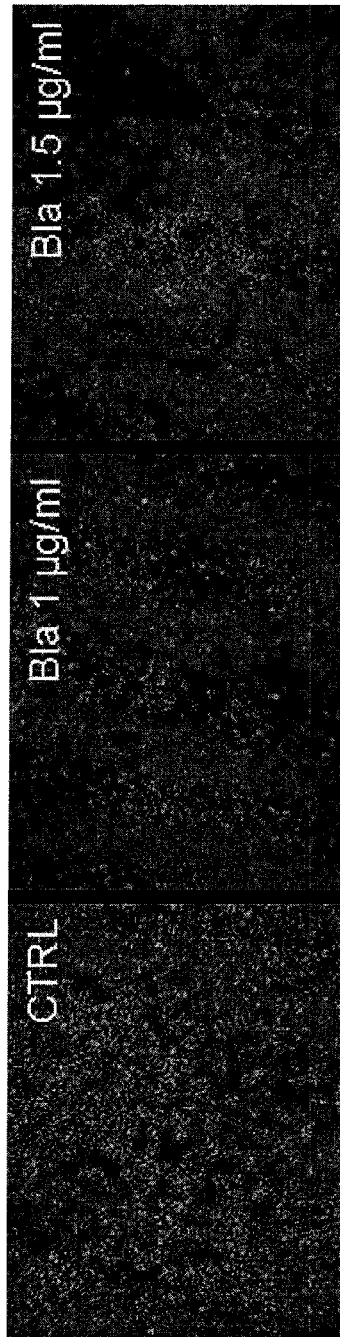
FIG. 2 shows SH-5YSY cells that were exposed to increasing concentrations of blasticidin.
Figure 2:
Figure 3:
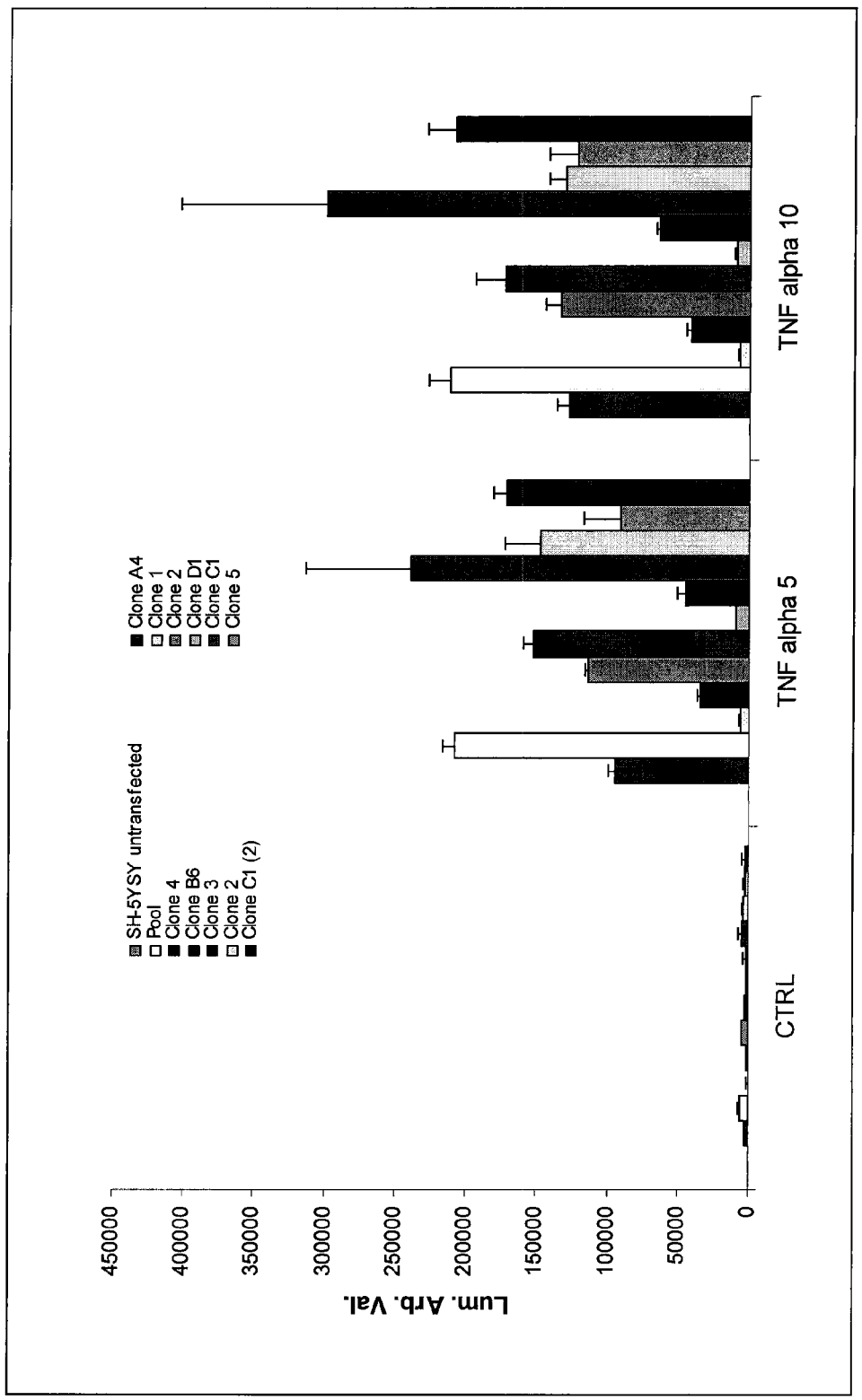
FIG. 3 shows the effect of TNF at 5 and 10 nM on the expression of the firefly lucipherase in different selected clones. Stimulation with TNF showed several high expressing clones. The clone C1 was the strongest expresser and was selected for further analysis.
Figure 4:
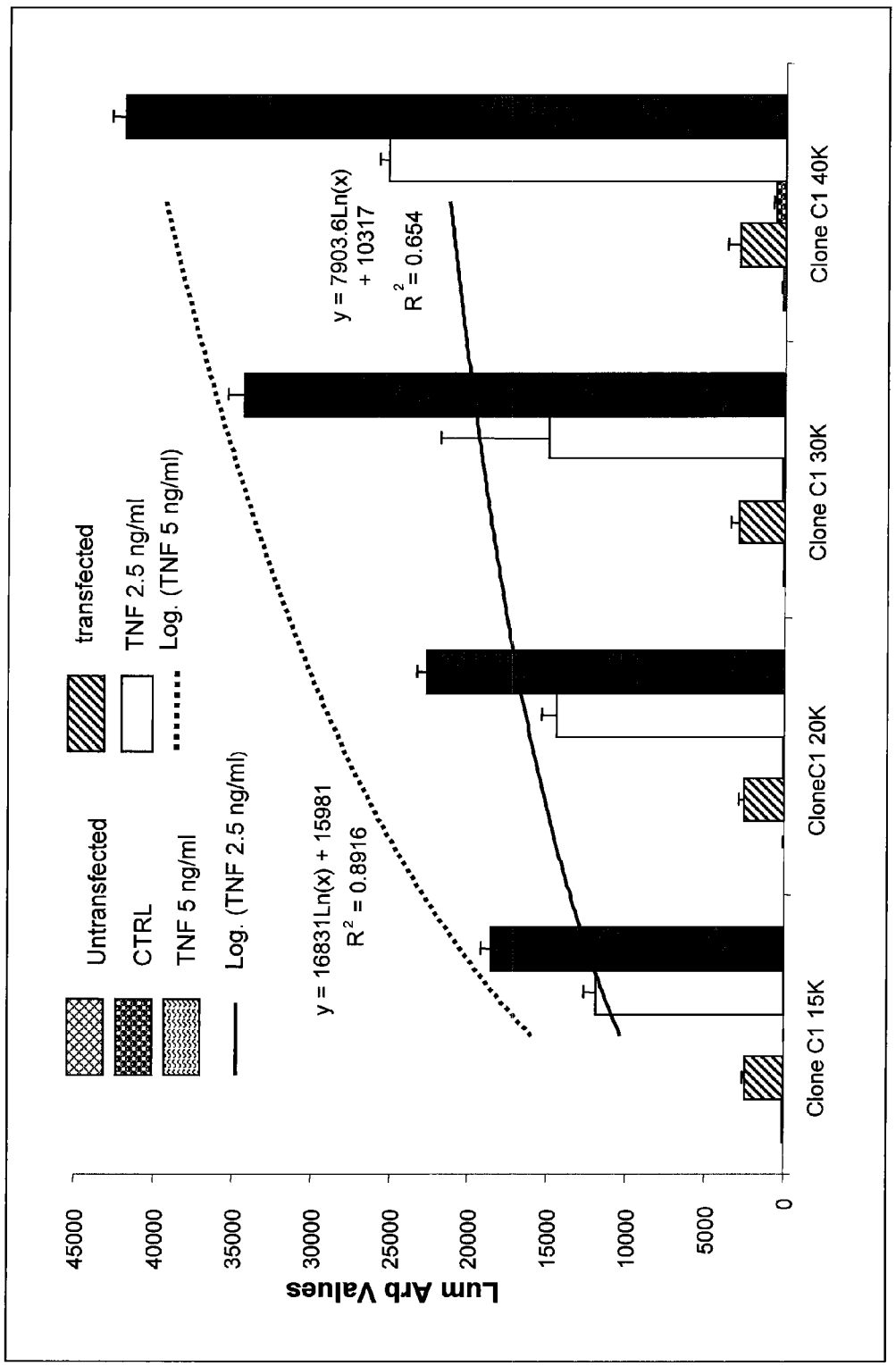
FIG. 4 shows the effect of different cell numbers and two TNF-α concentrations on luciferase expression in the clone C1.

SH-5YSY human neuroblastoma cell line was obtained from the American Tissue Culture collection (ATCC). The cells were expanded and frozen for long term storage. A commercially available expression vector containing the NF-kB promoter enhancer region driving the firefly lucipherase gene expression (see FIG. 1) was obtained. This plasmid was designed for transient expression studies and was devoid of any antibiotic-resistance conferring gene. A second plasmid containing the gene conferring resistance to blasticidin was also used. A dual transfection approach to obtain stable cell lines was employed. Prior to transfection, blasticidin sensitivity of the cell line was performed (See FIG. 2). It was determined that SH-5YSY cells were sensitive to the antibiotic toxicity and that 3 µg/ml caused total cell death (FIG. 2). After expanding and purifying adequate quantities of these plasmids, SH-5YSY cells were co-transfected with the above two plasmids and the clonal selection of the transfected cells in the presence of blasticidin proceeded. Several clones were identified that were both resistant to blasticidin and expressed the firefly luciferase upon exposure to TNF-α, a known inducer of NF-kB (See FIG. 3). After several assessments, a clone, C1, which expressed high levels of stimulated-luciferase expression and maintained it over time (see FIG. 3) was identified. To date, this clone has been in culture for over 37 passages without significant decline of the gene of interest induction. The optimal conditions for this assay to be carried out in a high throughput setting has been determined. Initially, the optimal number of cells needed was assessed. In FIG. 4 it is shown the effect of using a range of cells from 10,000 to 40,000. The data indicates that a sufficient dynamic range will be availale when using 20,000 cells/well. The assays has have been implemented using a similar cell density for HTS analysis without excessive problems. This cell line allows growing large scale quantities of cells fairly easily.

Figure 5:
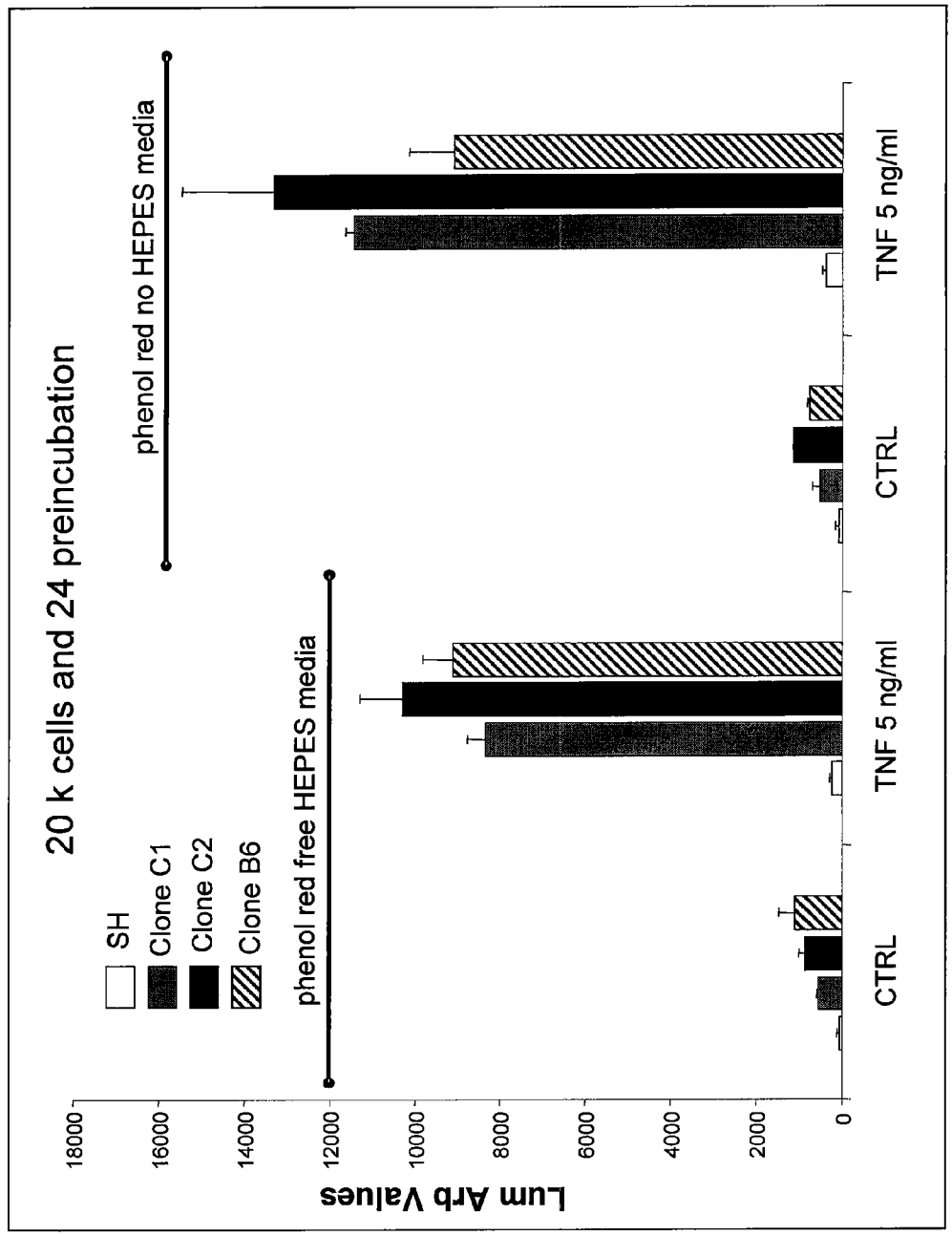
FIG. 5 shows a comparison between phenol red free HEPES-buffered DMEM and phenol red containing bicarbonate-buffered DMEM in C1 clone.
Figure 6:
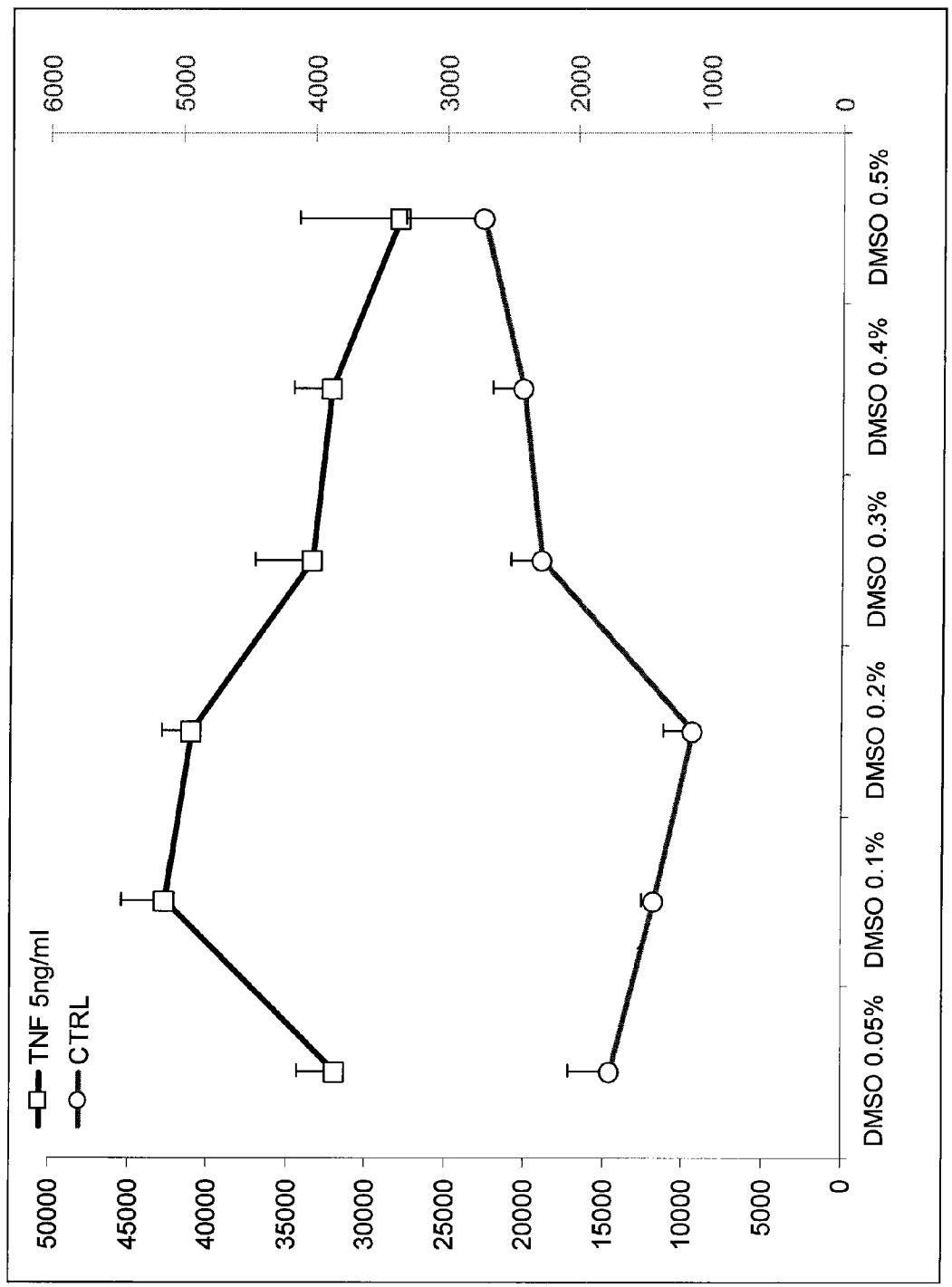
FIG. 6 is a graph illustrating the concentration-dependent effect of DMSO on TNF-induced lucipherase and on cell numbers in C1 clone.
Figure 7:
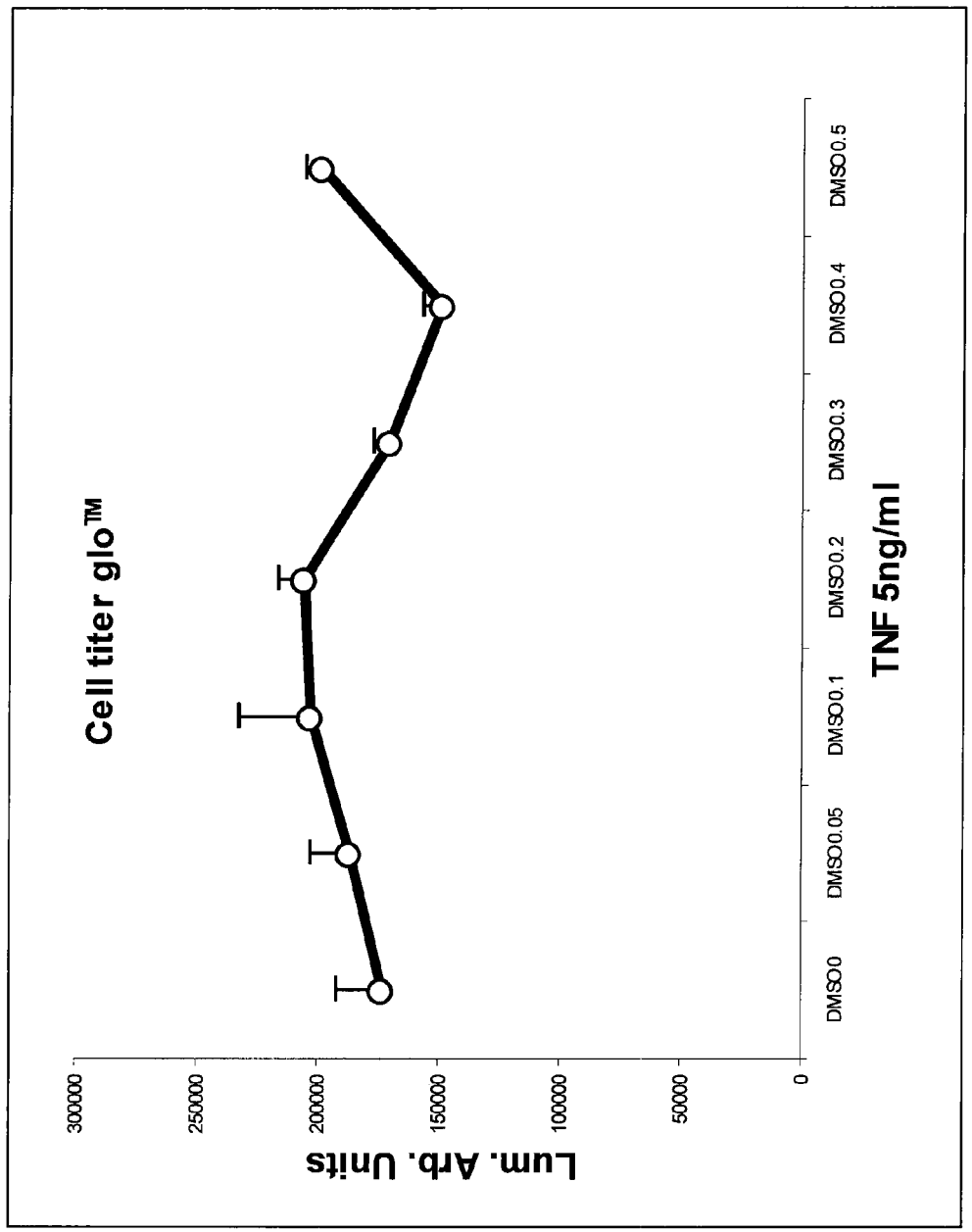
FIG. 7 is a graph showing the effect of increasing concentration of DMSO on the survival of the C1 clone cells. Cells were exposed to DMSO for 24 hours as they would in a screening run.
Figure 8:
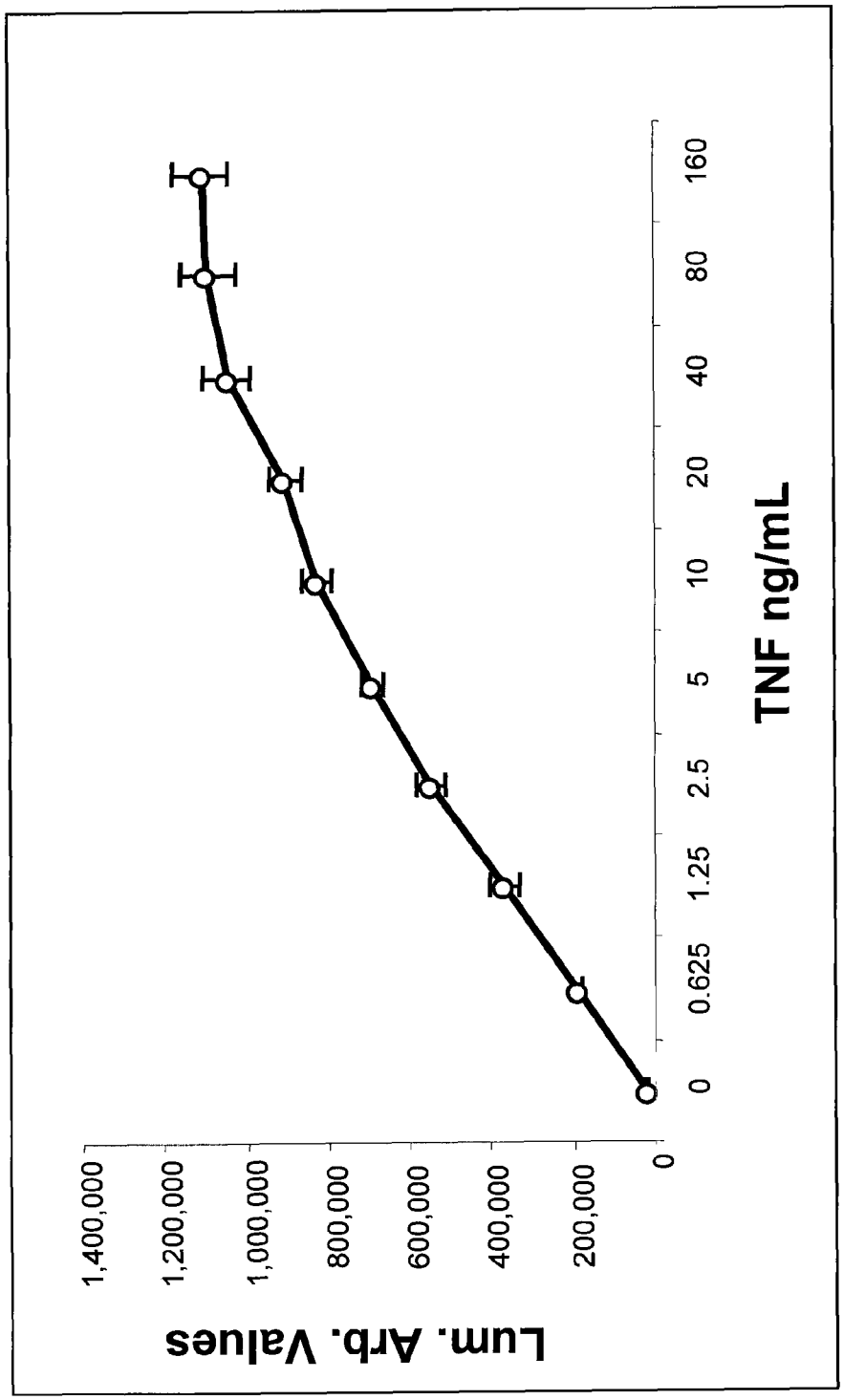
FIG. 8 is a graph showing the concentration dependent effect of TNF-α on NF-kB promoter driven luciferase expression.

Successively, the optimal time of incubation and media requirements were assessed. The data indicates that after a 24 hours settling time, exposure of the cells for 24 hours to positive controls such as TNF-α will allow for strong induction of the firefly liciferase (data not shown). These conditions are relatively affordable in HTS settings. Finally, since during robotic handling the plates containing the cells spend a significant amount of time outside the incubator and since phenol red could interfere with the reagents in the luciferase activity assay kit, the effect of using a phenol red free HEPES-buffered media was assessed. As shown in FIG. 5 there is a very little effect of phenol red free, HEPES-buffered media on the assay response and dynamic range. Therefore, the assesment is that it is possible to run this assay using these more forgiving media. Since the compounds contained in the most commonly used libraries are dissolved in DMSO, the effect of DMSO on both luciferase expression in response to TNF-α and C1 clone survival during assay simulations was characterized. The effect of increasing concentration of DMSO ranging from 0.05% through 0.5% on TNF-α induction of luciferase (black line and black scale) is shown in FIG. 6. Also the effect of DMSO on baseline expression of luciferase in the C1 clone is shown in FIG. 6 (gray line and gray scale). In FIG. 7, it is shown the effect of DMSO on cell survival in the same conditions described in FIG. 6. In these experimental settings cells, settled for 24 hours, and then were incubated for an additional 24 hours with DMSO at the indicated concentrations. At the end of the incubation phase cell viability was assessed using the commercially available kit Cell Titer Glo™ following the manufacturer instructions (Perkin Elmer). Results reported in FIG. 7 indicate that DMSO up to 0.5% does not affect either cell viability or TNF-α induction of the luciferase reporter. Finally, the effect of different concentrations of TNF-α was studied in the clone C1. Increasing the concentration of TNF-α from 0.625 up to 40 ng/ml caused a linear increase of the luciferase expression in C1 cells. Further increase in TNF concentration did not cause any additional increase of luciferase activity. This indicates that during the screen that compounds able to activate the promoter with different efficiency will be easily picked up by our detection system (FIG. 8).

Figure 9:
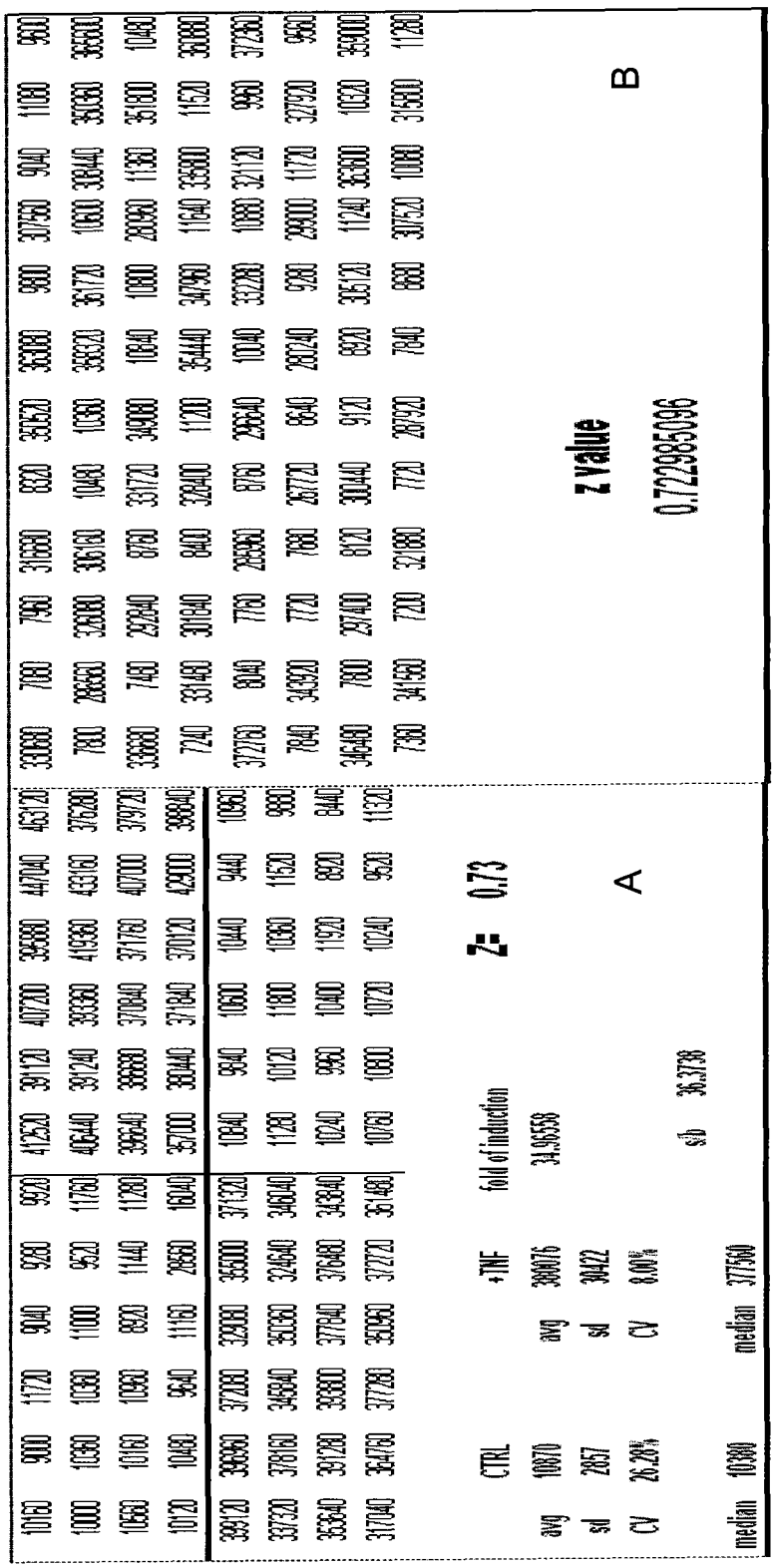
FIG. 9 gives examples of Z' plate arrays and results. In panel A cells were laid out in a plate and then exposed to vehicle or to 5 ng/ml TNF for 24 hours. Treatments were performed in ¼ quadrant with a cross pattern. In these settings Z' values above 0.7 have consistently been performed. In panel B instead of a quarter arrays, control and TNF treated cells were scattered across the plate. Even in this random pattern Z' values were consistently above 0.7.

Essential to development of an assay for high throughput screening is the assessment of Z' values. This statistical parameter assesses the possibility that data obtained in a single well are statistically significant. In general, assays can generate negative and positive Z' values. Negative Z' values indicate a very unpredictable assay. Z' values comprised between 0 and 0.5 indicates an assay with a certain degree of uncertainty. Finally Z' values above 0.5 indicate very robust assays. Z' values above 0.7 both in canonical quadrant Z' plates arrays and in scrambled Z' plates arrays have been produced consistently in laboratory settings (see FIG. 9). This indicates that the assay is very robust.

Figure 10:
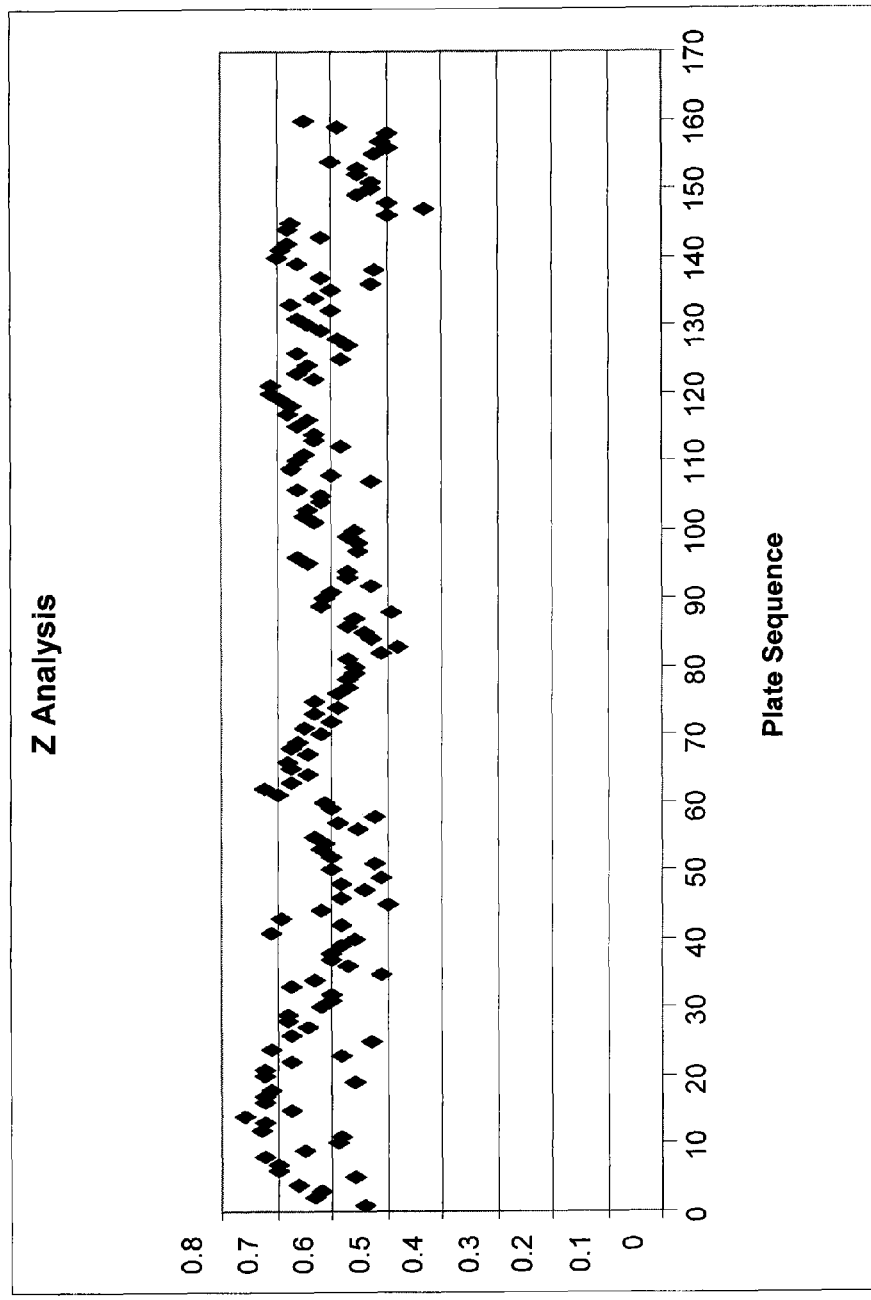
FIG. 10 is a collection of Z' values determined on a robotic platform during a screening campaign; Z' values were always consistent with a very robust assay.

This assay has been adapted to 96-, 384-, and 1536-well plate format. Higher density formats are also possible. A high throughput screening campaign of 300,000 compounds in 1536-well format has been conducted successfully. FIG. 10 depicts the Z' values for the 160 plates used.

Figure 11:
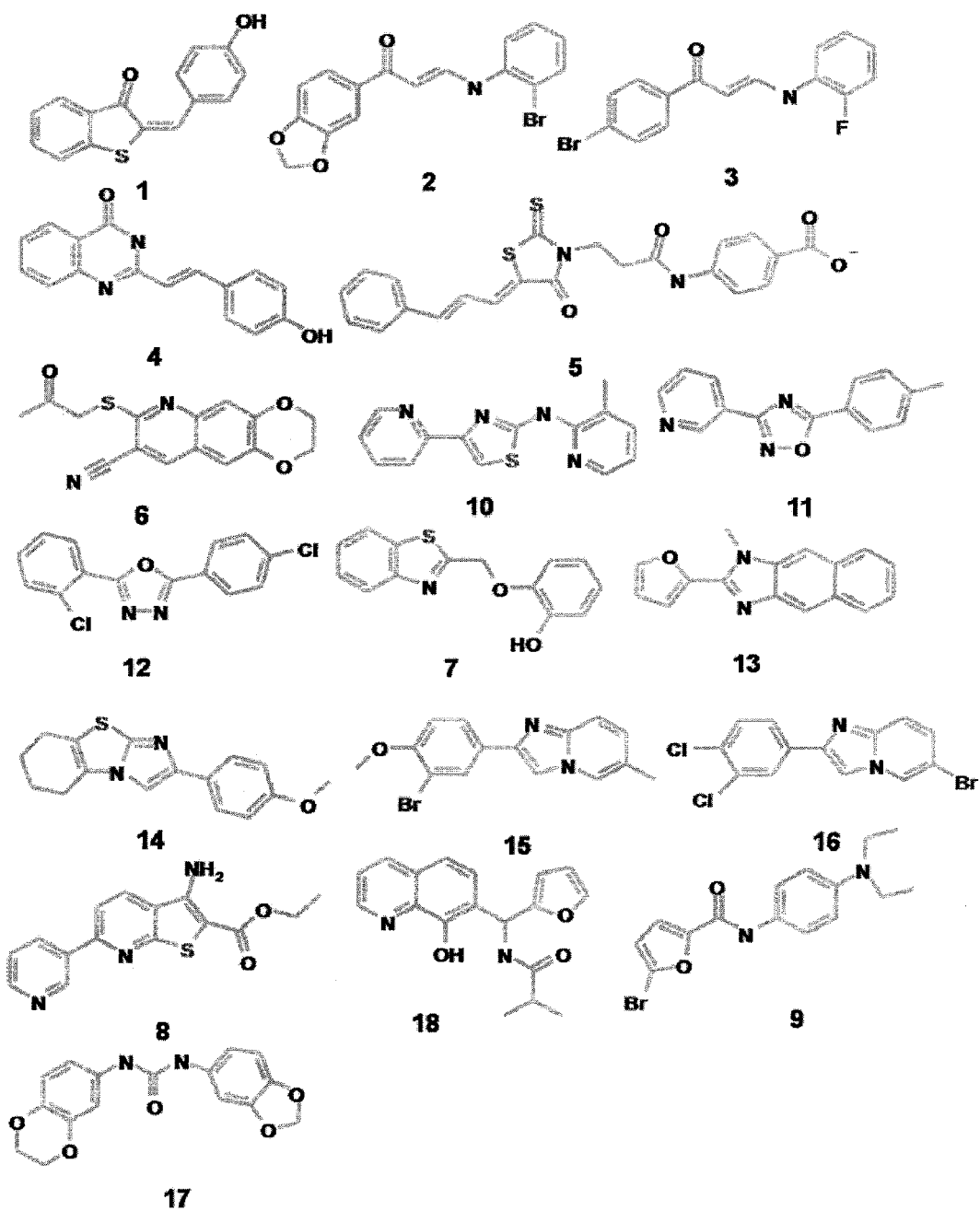
FIG. 11 shows structures of specific compounds selected for further follow up testing.
Figure 13:
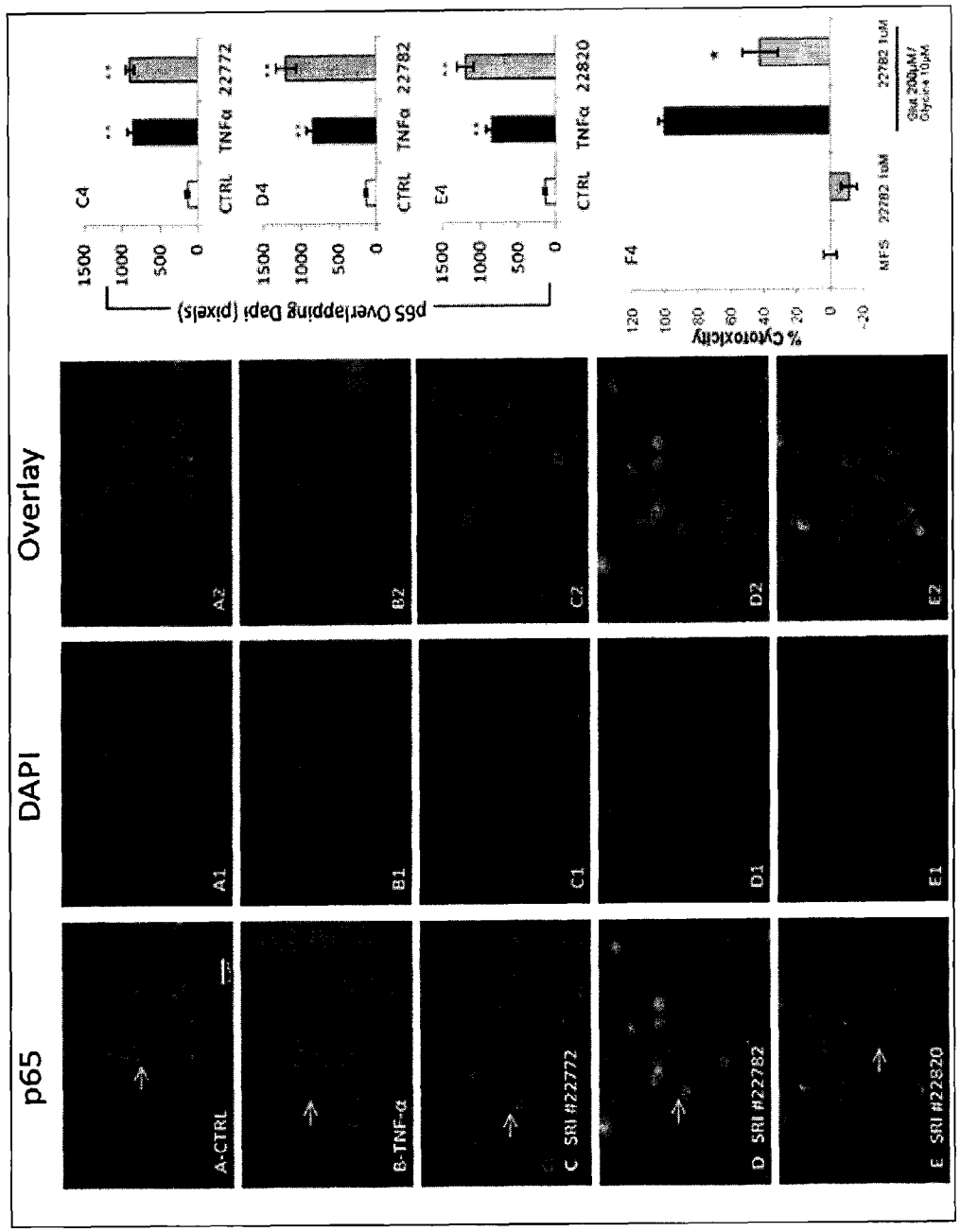
FIG. 13 shows the activation of NF-kB p65 in primary neurons. Nuclear translocation/activation of NF-kB p65 in response to the indicated CMPDs after 24 h exposure is shown and compared to control and TNF-α (24 hours) treated cells. Examples of nuclear p65 are highlighted by the arrows. Image analysis allowed us to quantify the data and perform statistical analysis. A significant increase of nuclear presence of p65 is shown in the bar graphs in panels C4, D4 and E4. Panel F4 shows the neuroprotective effect of CMPD 22782 as a prototype compound.
Figure 14:
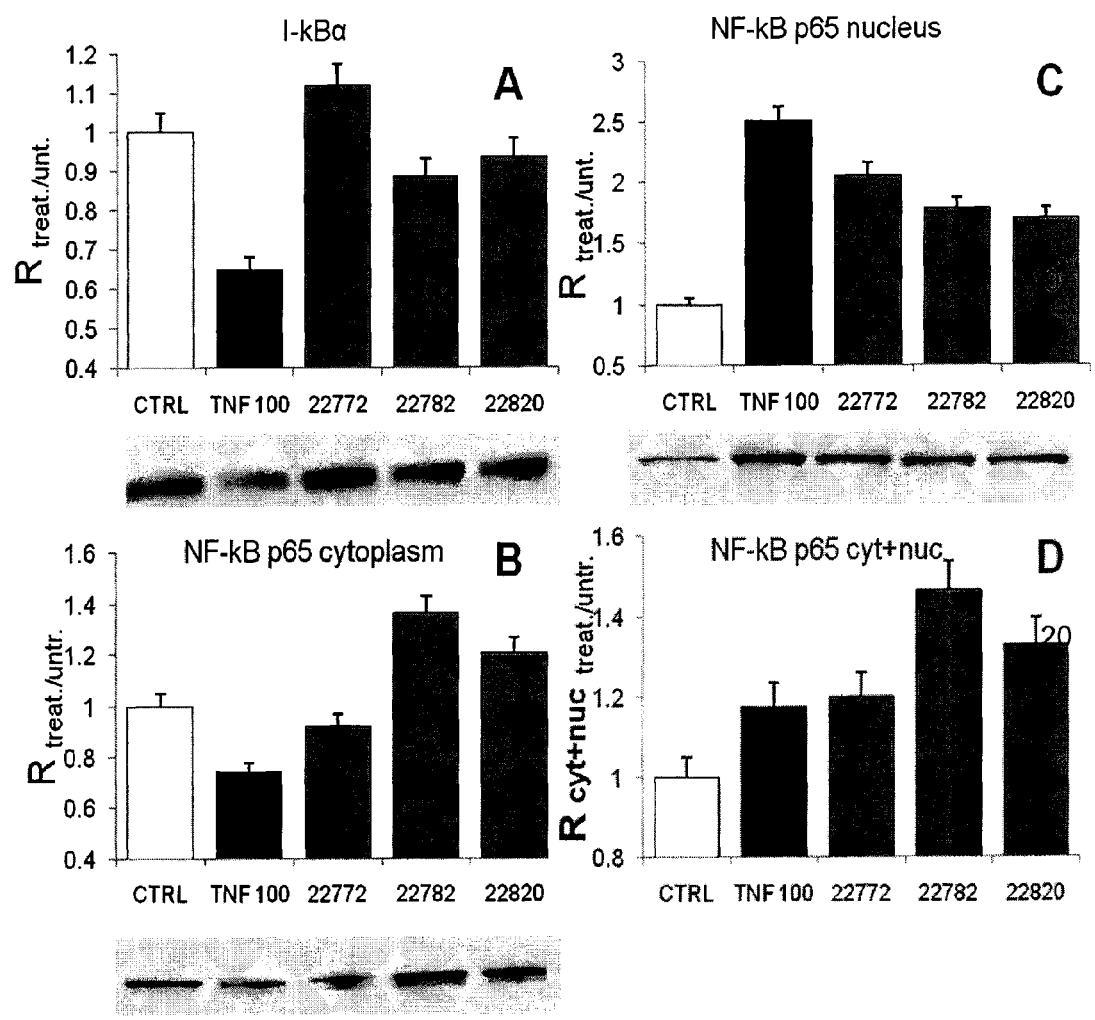
FIG. 14 shows the effect of prototype CMPDs on I-kB and NF-kB p55. A) I-kB was not affected by CMPD exposure while it was reduced by TNF. B) CMPDs increased cytoplasmic NF-kB p65. C) CMPDs increased nuclear localization of NF-kB p65. D: The sum of CMPD effects on P65 in the cytoplasm and in the nucleus.
Figure 15:
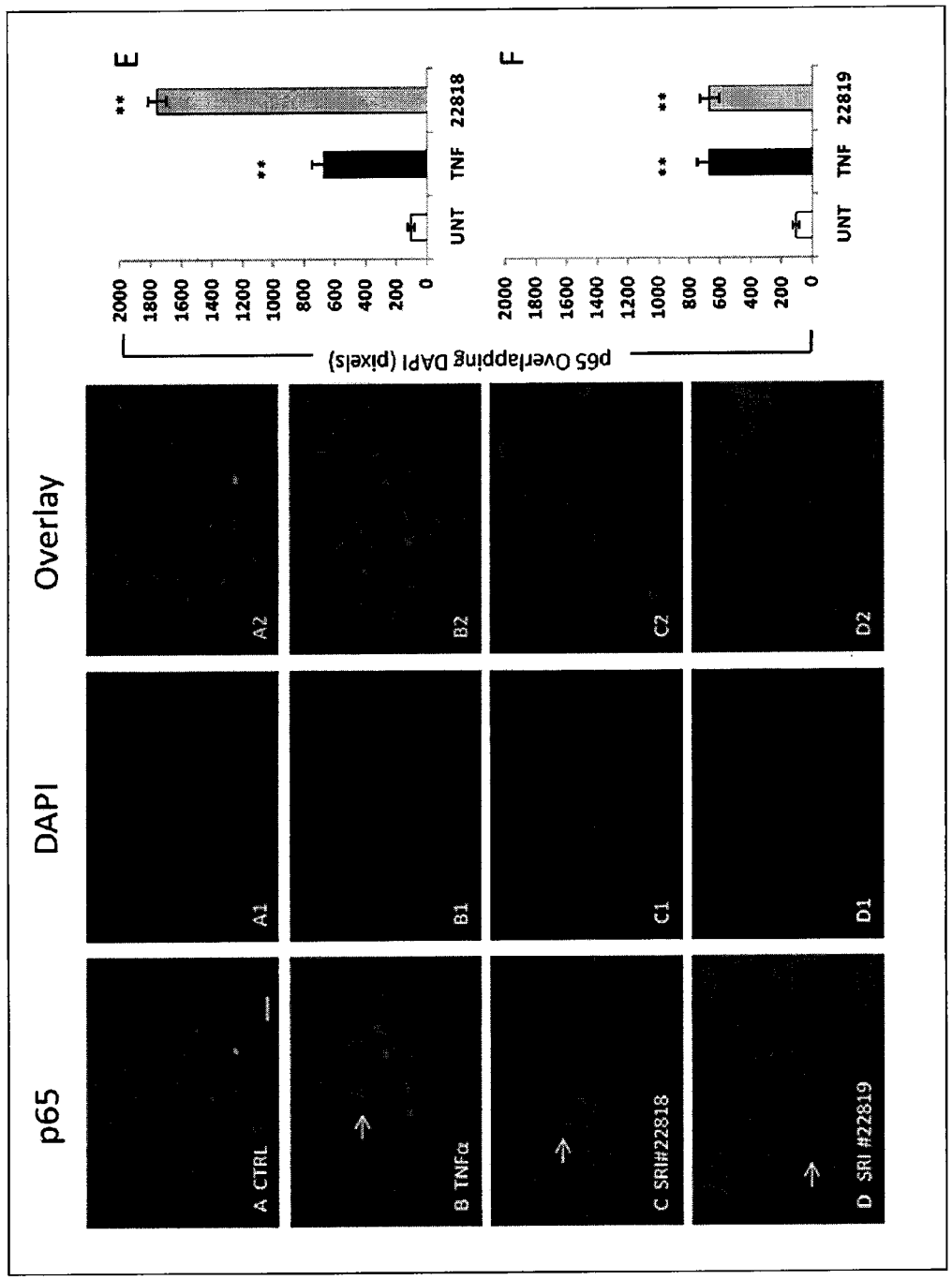
FIG. 15 shows the activation of NF-kB p65 in primary neurons by neuron selective CMPDs. Nuclear translocation of NF-kB p65 in response to CMPDs after 24 h exposure is shown in and compared to control and 100 ng/ml TNF-α (15 min) treated cells. Examples of nuclear p65 are highlighted by the arrows. Image analysis allowed quantification of the data and statistical analysis. A significant increase larger or equal to the strong effect of TNF of nuclear p65 is shown in panels E and F for the CMPDs.

In addition, the data shows that a number of compounds are selectively effective in neurons, that they increase MnSOD activity and that they are neuroprotective on two different neurodegenerative in vitro paradigms. In particular, the data indicates activation of NF-kB p65 in astrocytes by 8 of the 18 compounds, shown in FIG. 11. Also shown are additional compounds that were inactive in astrocytes, but are able to increase NF-kB-driven MnSOD activity in primary cortical neurons in culture. MnSOD is a key enzyme in inactivating ROS, the end point of almost all neurodegenerative insults. This enzyme is under the direct control of NF-kB as shown in the literature. Therefore, increased MnSOD activity can be a reporter for NF-kB activation and a reliable indicator of neuroprotective activity. Compounds SR122772, 22774, 22773, 22780, 22782, 22817, 22820, 22864 (see FIGS. 11 and 12) were able to activate in an expression-dependent manner NF-kB p65 in primary astrocytes. It has now been found that compounds deemed inactive in astrocytes, are able to increase NF-kB-induced MnSOD activity and expression in primary neurons. Compounds SR122781, 22818, 22776, 22819 were all active in neurons but not in astrocytes. Only SR122777 thus far is inactive in these assays.

Figure 16:
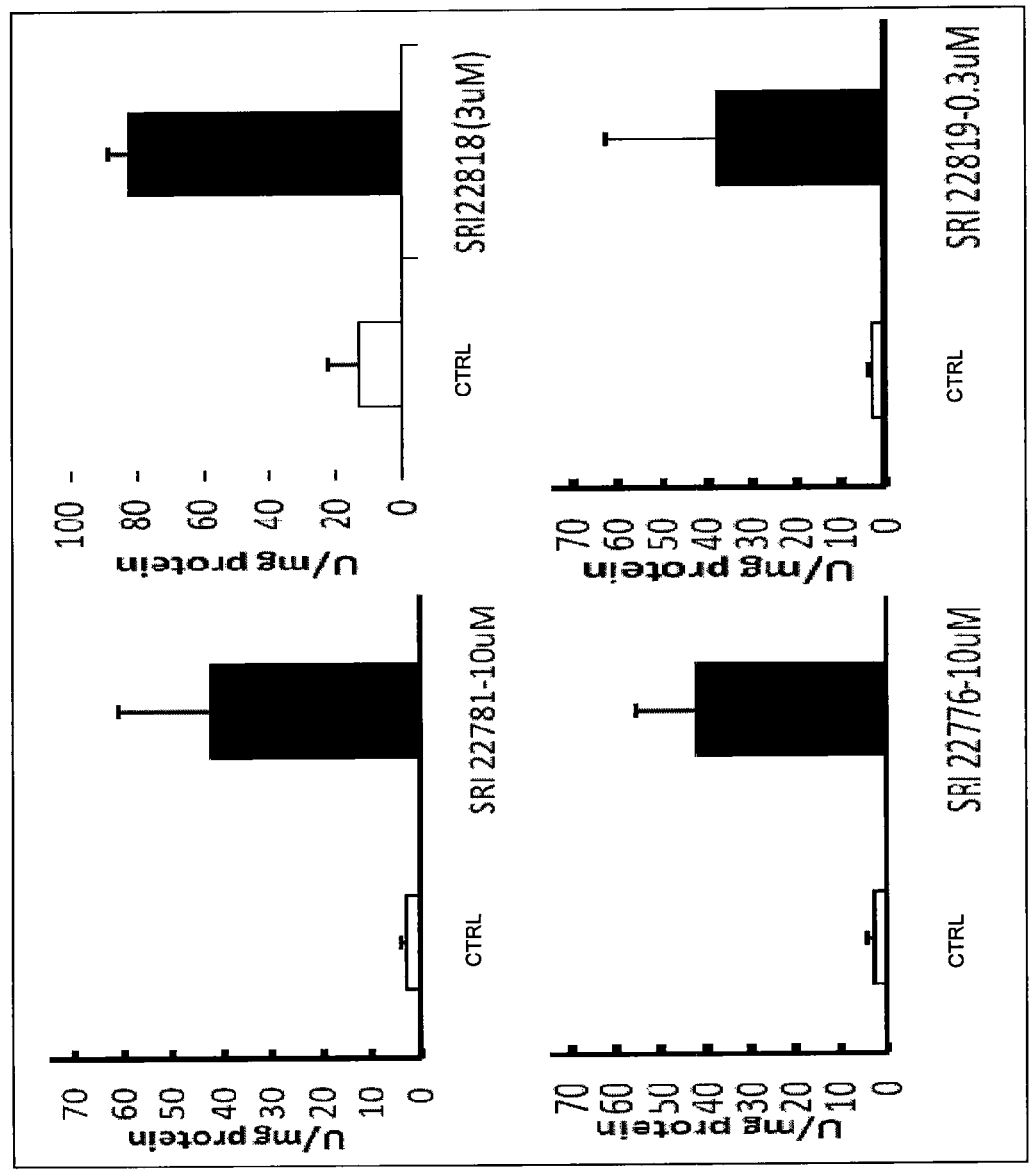
FIG. 16 is a four graph collection showing the effect of 4 of the compounds included in this document as prototype on the induction of MnSOD a neuroprotective enzyme that is actuated by NF-kB induction.
Figure 20A:
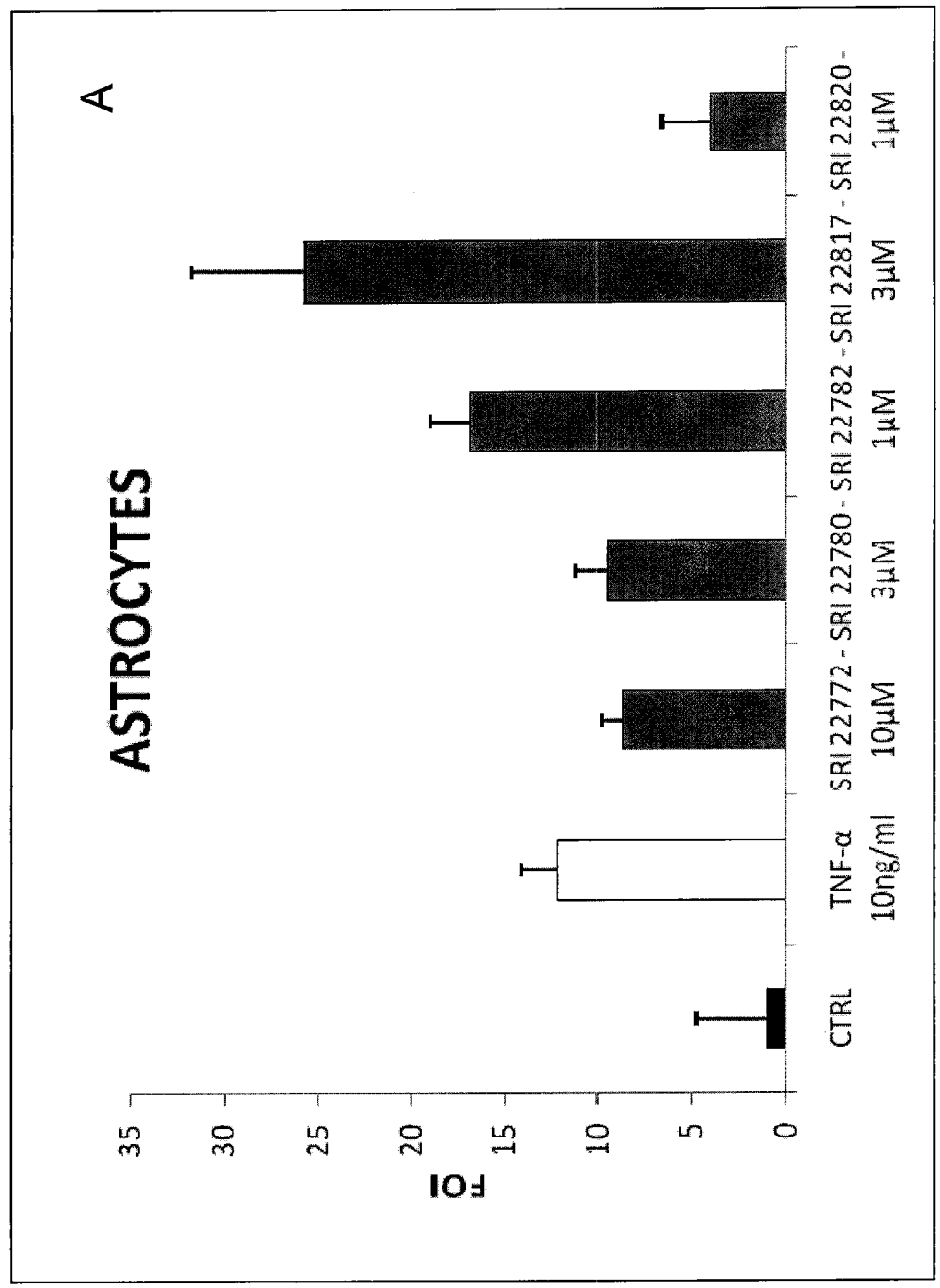
FIG. 20 shows the effect of CMPD on MnSOD activity in primary neurons. A) CMPDs active in astrocytes increased activity of MnSOD activity in primary neurons. B) CMPDs inactive in astrocytes also increased NF-kB driven MnSOD expression\activity in neurons.
Figure 20B:
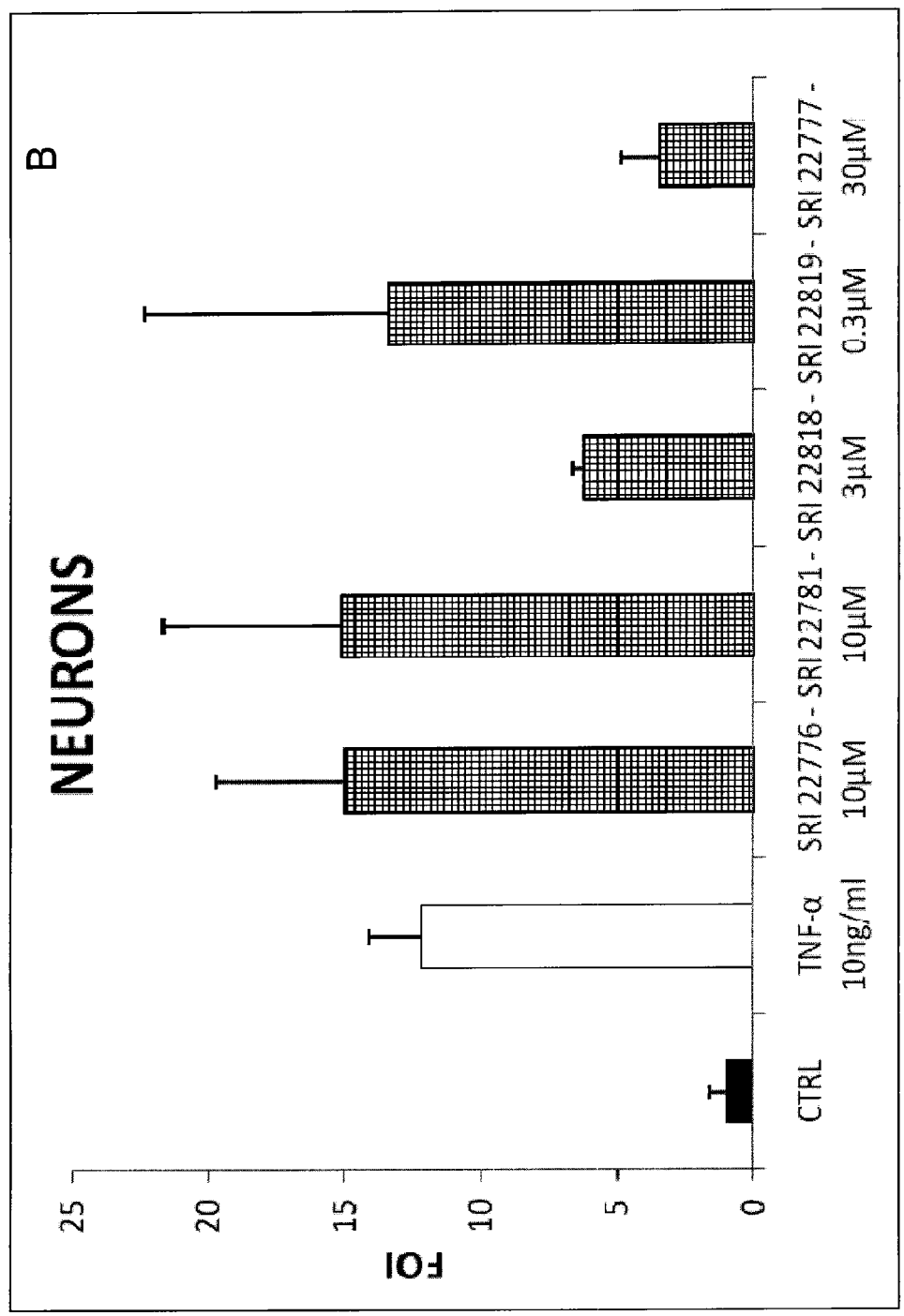
Figure 22A:
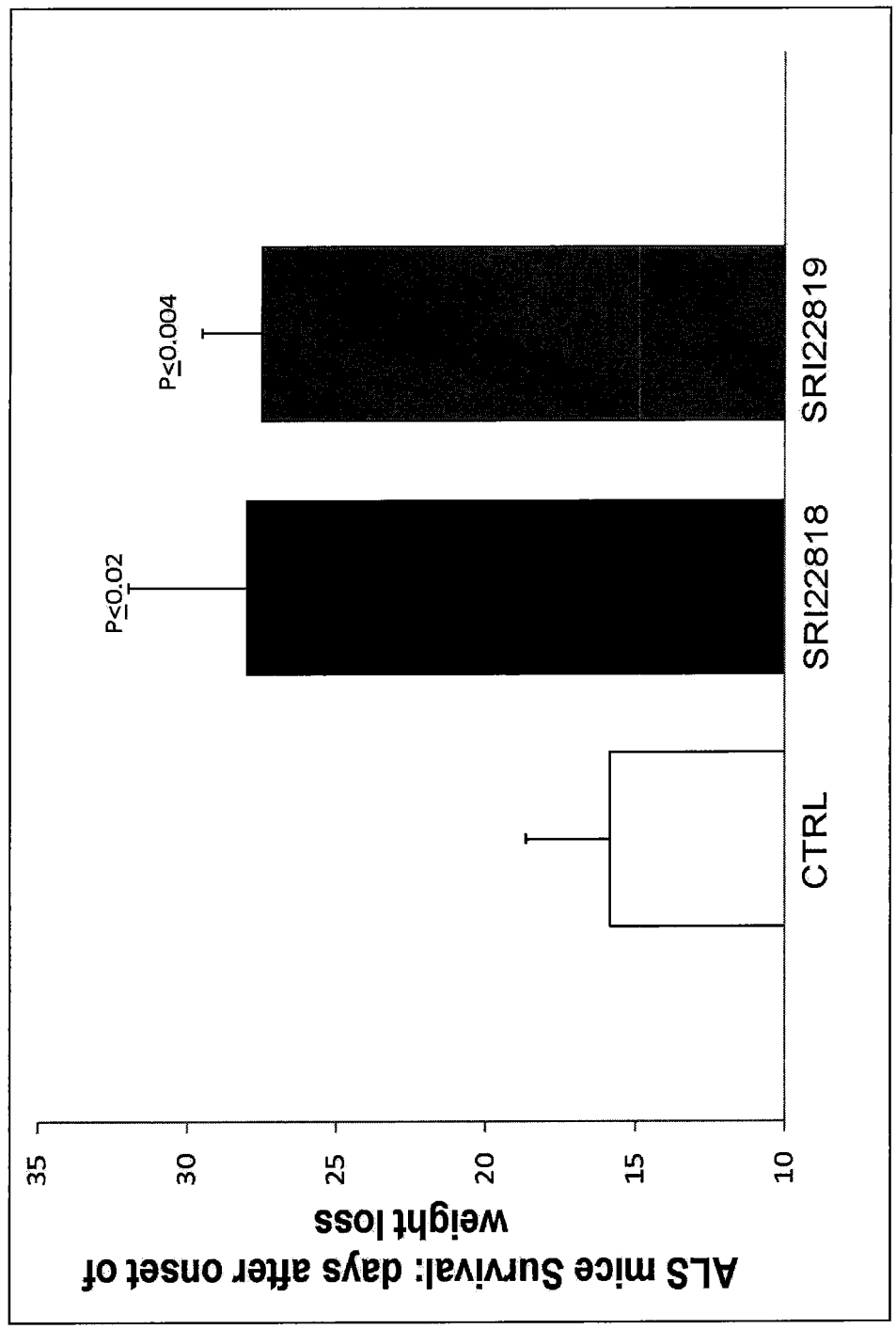
FIG. 22 shows the effect of treatment with SR122818 and 22819 on development of ALS-like symptoms in G93A mice. A) Shows that survival was significantly improved in animals treated with both CMPDs; B) shows that reaching the 50% death threshold was significantly delayed; C) shows that the onset of the symptoms is slightly affected, whilst progression through the 4 neurological grades was greatly delayed; and D) shows that the weight loss due to muscle atrophy is also significantly delayed in animals treated with the two CMPDs.
Figure 22B:
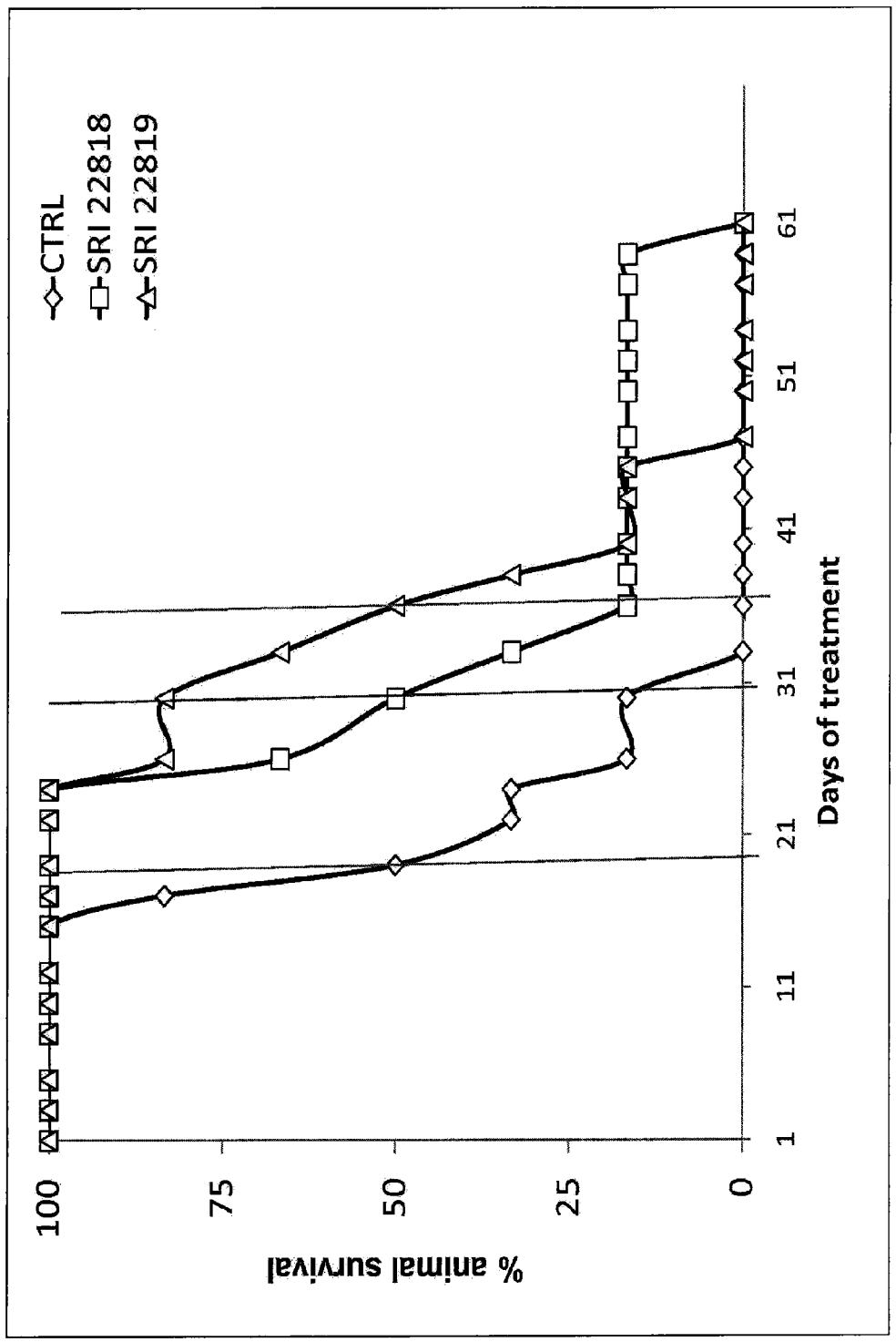
Figure 22C:
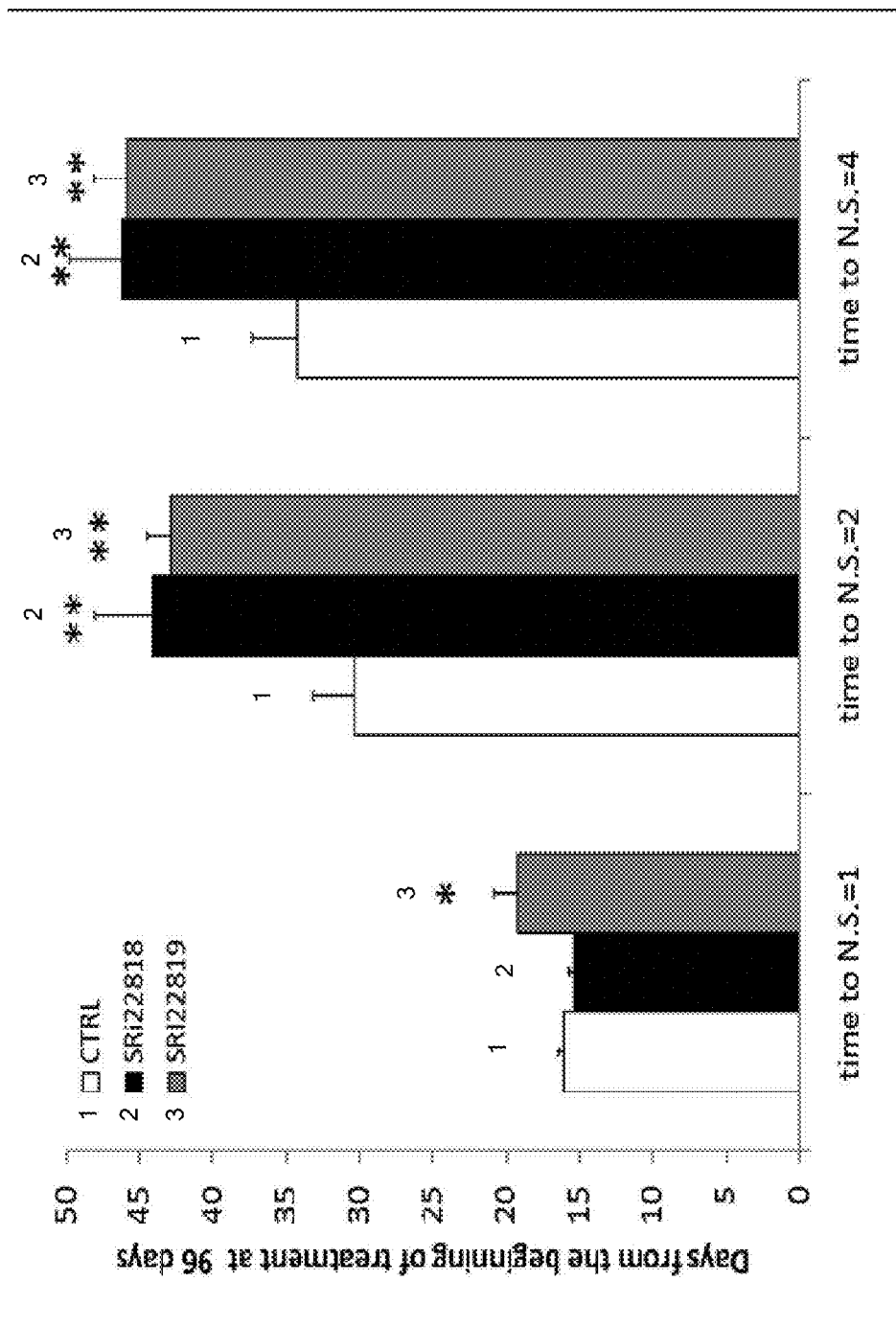
Figure 22D:
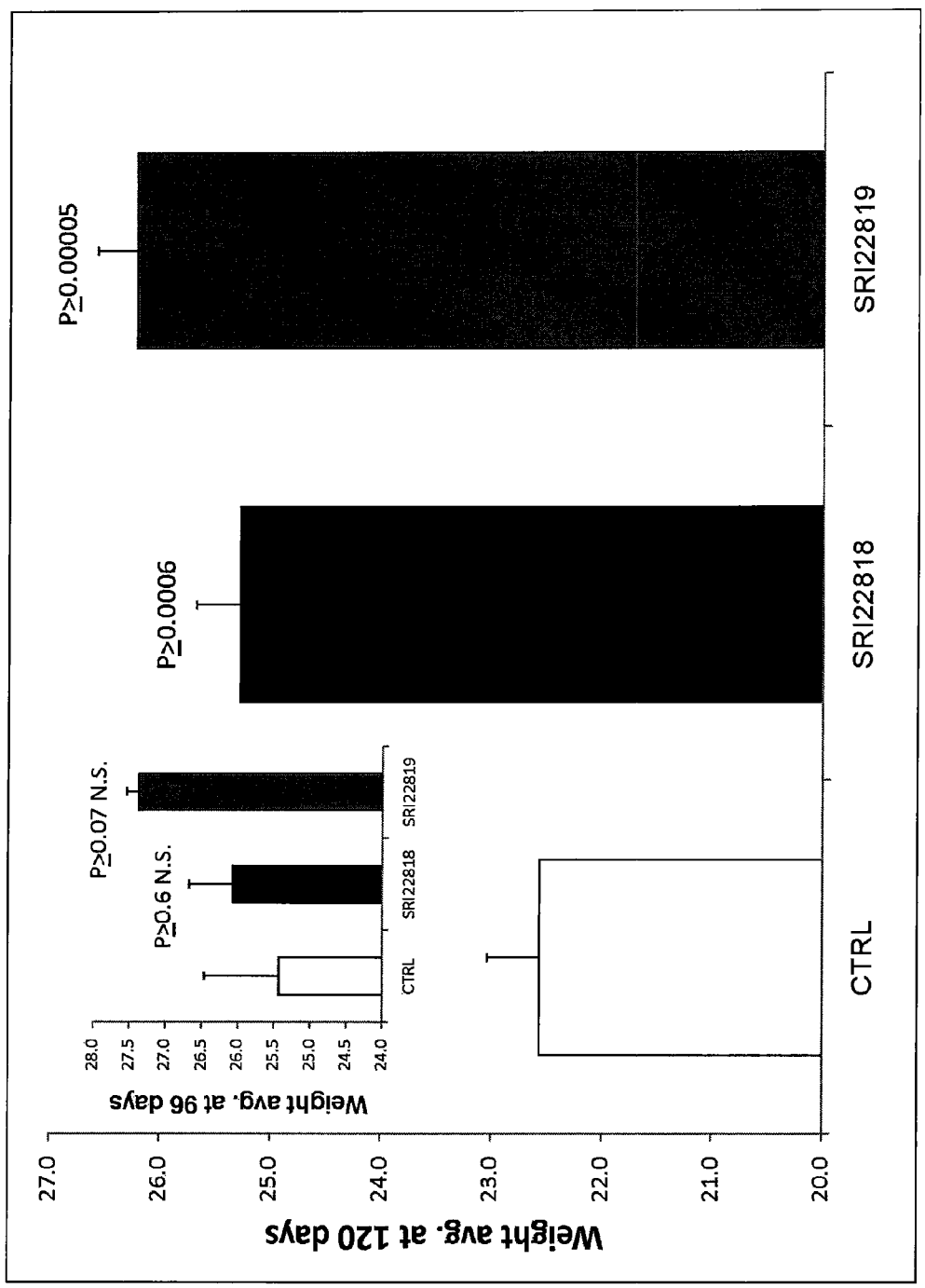

All compounds belonging to the group of active in astrocytes tested thus far in the MnSOD activity assay increased MnSOD activity in neurons. In fact, compounds 22817, 22780, 22782, 22820 were able to induce a large increase of MnSOD activity in primary neurons. On the other hand, compounds SR122781, 22818, 22776, 22819 belonging to the group of compounds inactive in astrocytes, were able to increase NF-kB-induced MnSOD activity in primary neurons (see FIGS. 16 and 20B). The discovery of these neuron-selective compounds suggests the possibility that compounds exist that activate NF-kB p65 in neurons but not in astrocytes. This feature could be important since activation of NF-kB in astrocytes could have unwanted effects. However, it needs to be pointed out that the final effect of NF-kB activation in glial cells is unknown at this stage and does not represent a disqualifying factor for active compound selection. Regardless, having compounds active in neurons which are not active in astrocytes can be a very important and interesting aspect of our research. In FIGS. 16 and 20B, it is shown the effect of the four above mentioned compounds on MNSOD expression in primary neurons. At the concentration tested, the compounds were as potent as or more potent than TNF-α (an extremely powerful inducer of MnSOD). Stimulation of MnSOD activity by the compounds exceeded 11 folds of the basal enzyme activity.

Figure 17A:
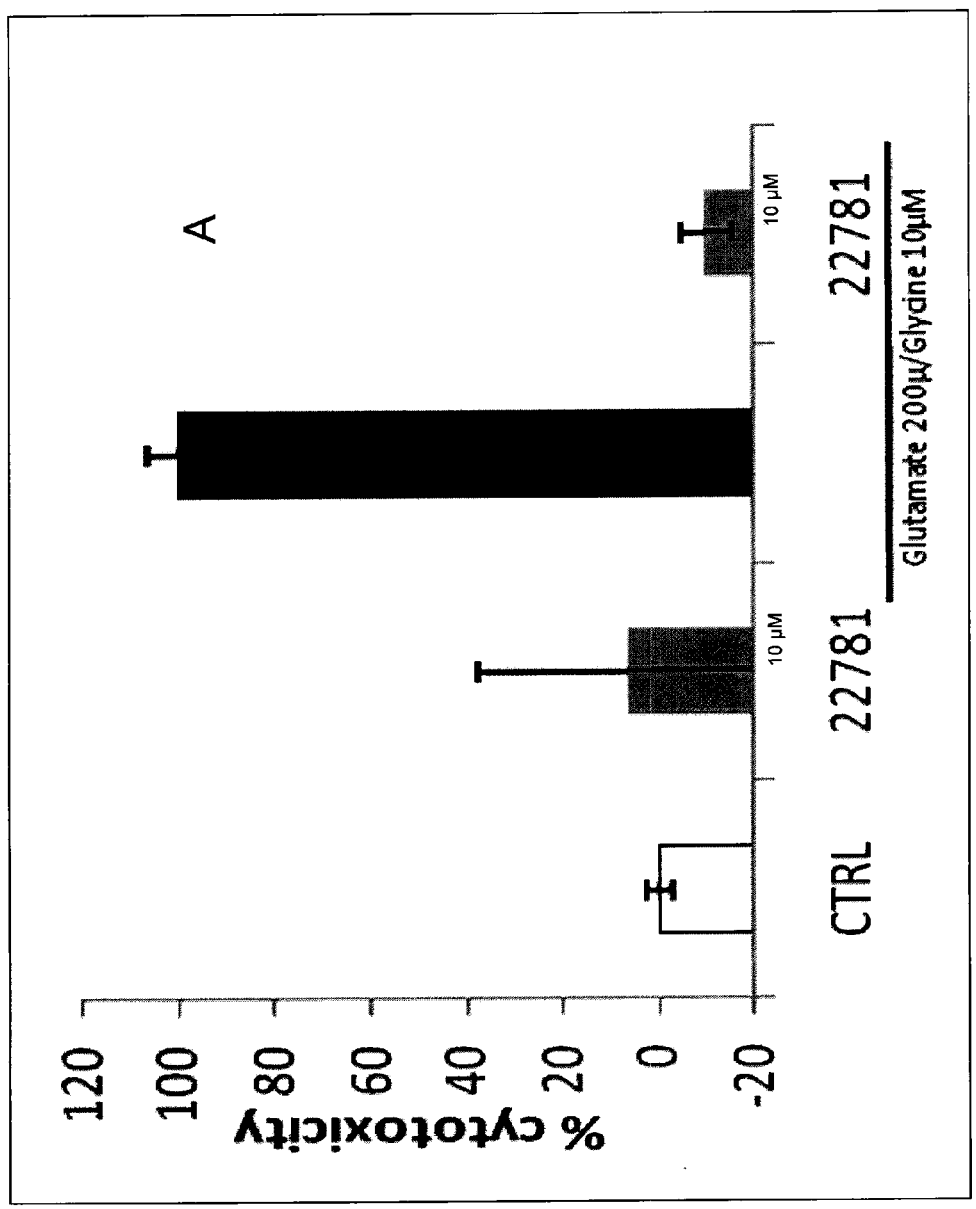
FIG. 17 (A-C) shows the neuroprotective effect of prototype compounds according to the present disclosure on three well established in vitro models of neurodegeneration that are widely use to test in vitro effective compounds.
Figure 17B:
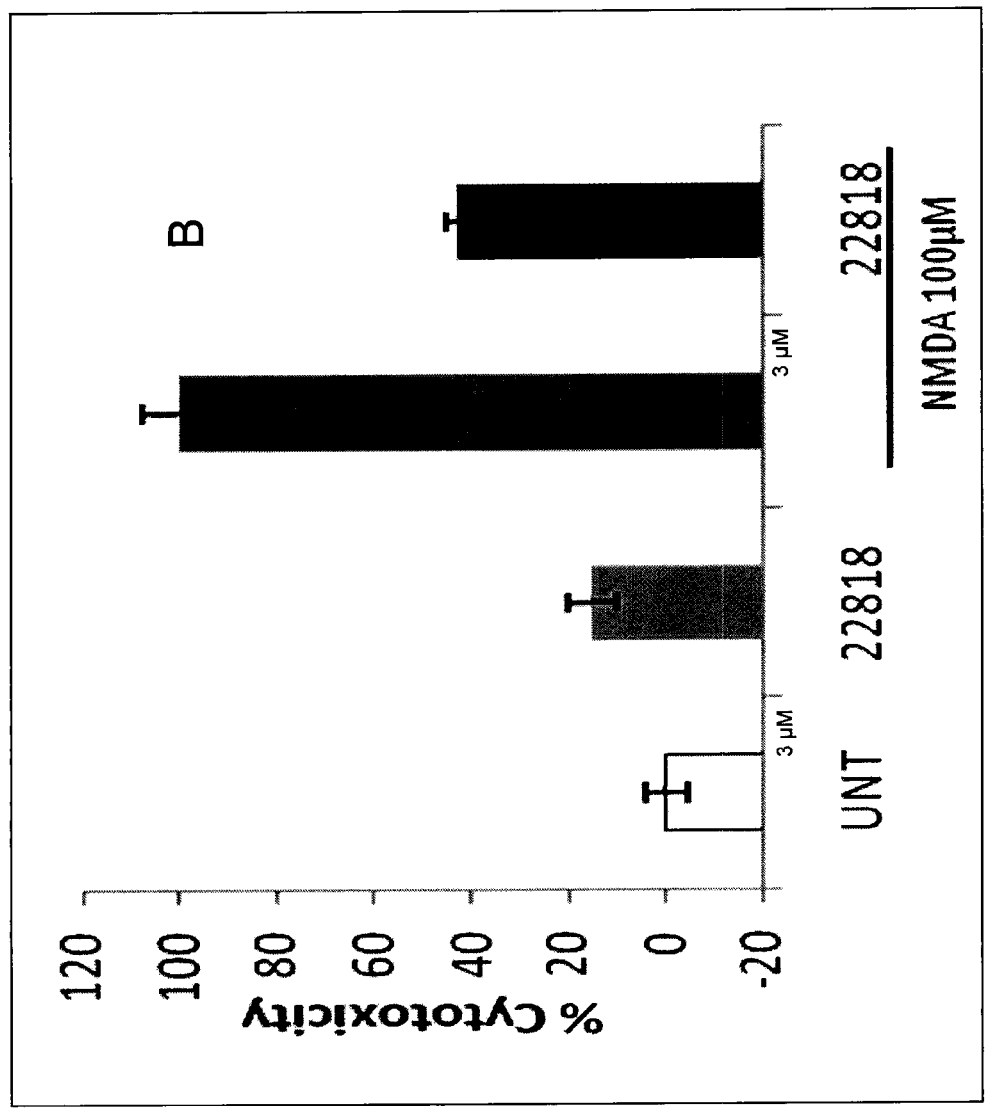
Figure 17C:
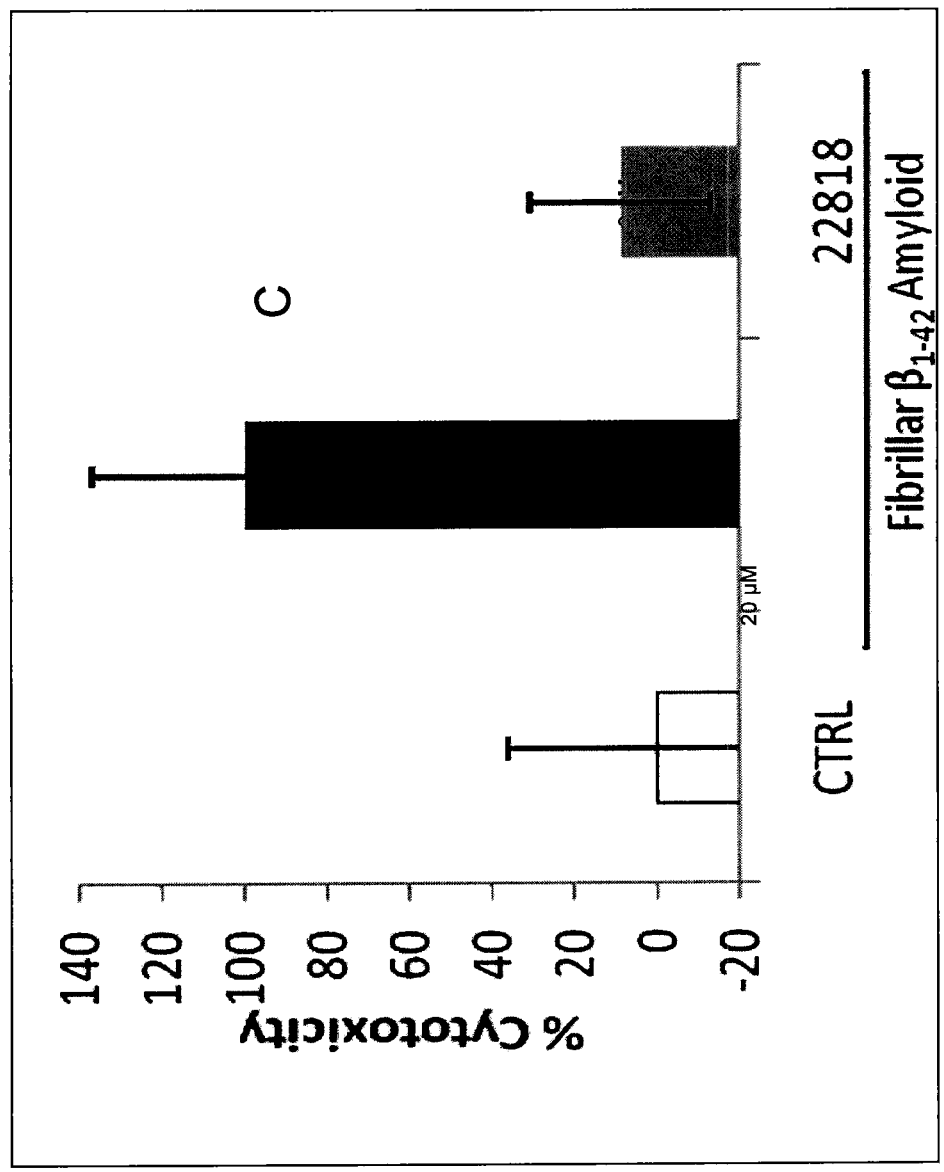
Figure 18:
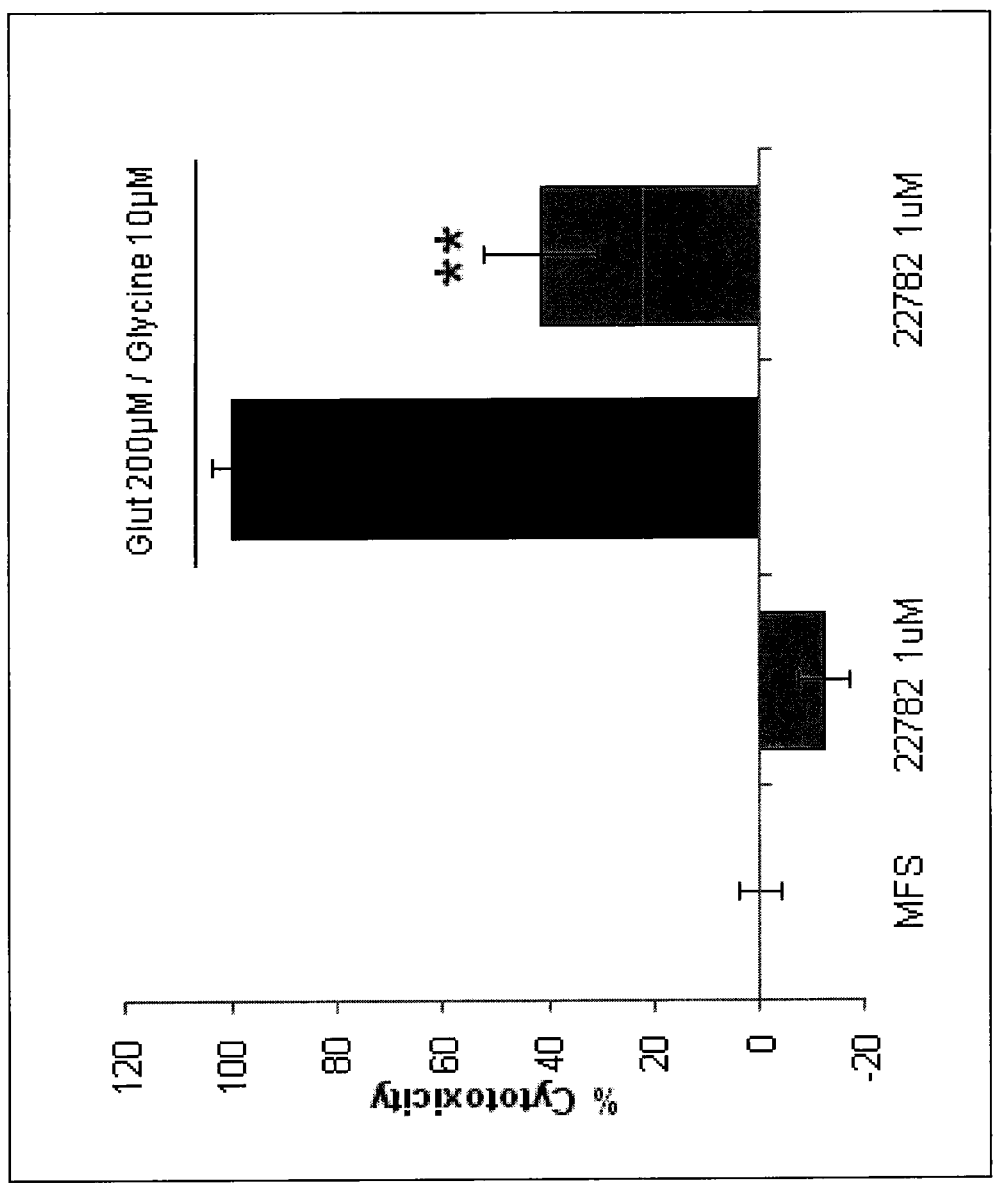
FIG. 18 shows the effect of the indicated compound on the toxic effect of glutamate in primary neurons. The data indicate that 60% of the cell death induced by glutamate is prevented by the compound 22872.
Figure 19:
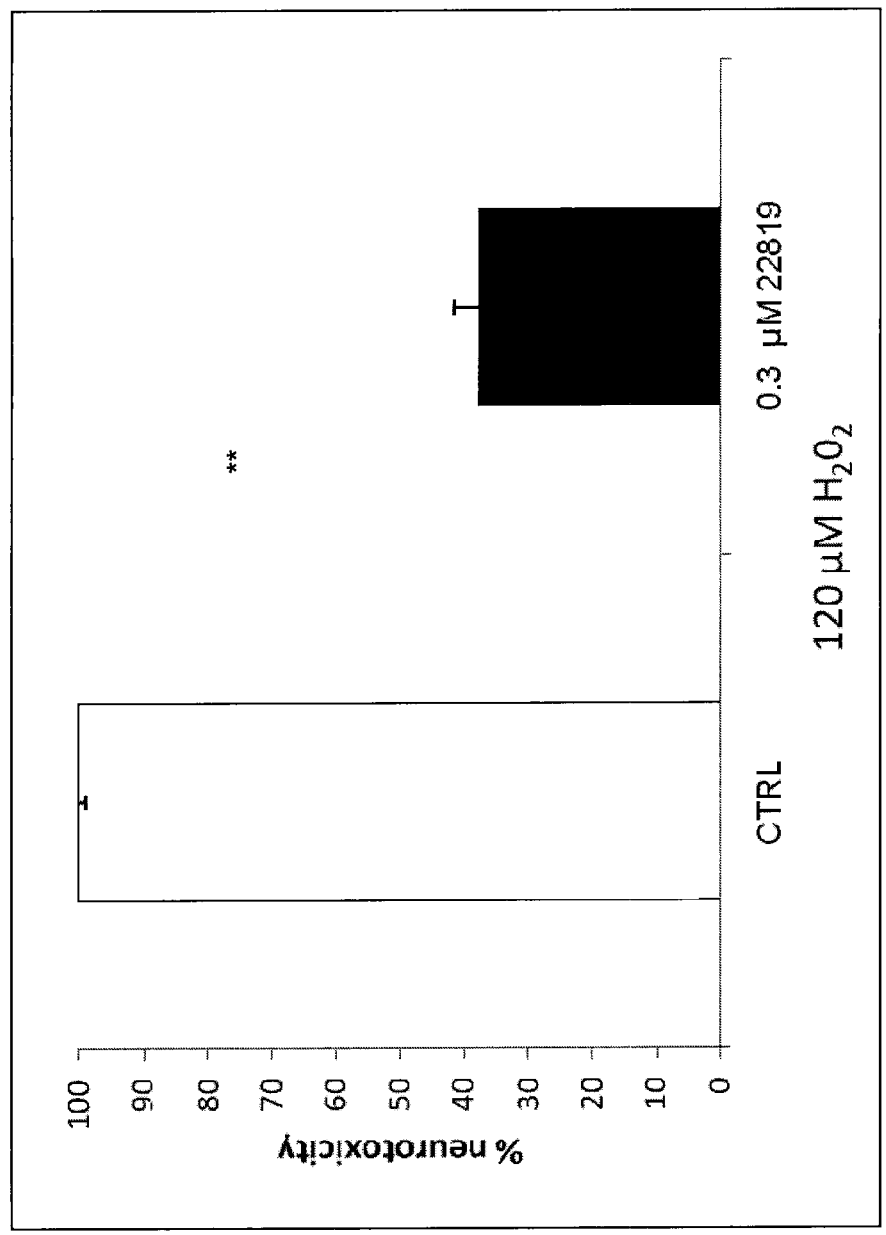
FIG. 19 shows the effect of CMPD 22819 on neurotoxicity induced by $H_2O_2$. Primary rat cortical neurons at 6 D.I.V. were pretreated for 24 hours with 300 nM of 22819 and exposed to toxicity by 120 μM of $H_2O_2$. Neurons pretreated with the CMPD showed a 62% reduction of the $H_2O_2$ induced toxicity.

Neuron selective compounds SRI22781 and SRI 22818 show neuroprotective features in vitro. These two compounds belonging to the active in neurons but inactive in astrocytes category cause protection of neurons in different paradigm toxicity experiments. These two compounds, which are the only two tested, selectively increase NF-kB-driven MnSOD activity in neurons but do not activate NF-kB p65 in astrocytes. In panel A of FIG. 17, it is shown the protective effect of compound SRI22781 on glutamate excitotoxicity. Primary neurons pretreated with our compound for 1 hour were exposed to a toxic concentration of glutamate in the presence of glycine and in absence of magnesium for 1 hour and then replaced with their original culture media containing the compound and incubated for additional 24 hours in the presence of the compound or vehicle. At the end of the experimental period, the cells were analyzed using standard image-based or biochemical viability assays. In Panel A, it is shown that SRI22781 had no direct toxic effect and that glutamate caused significant cell death. However, cells pretreated with SRI22781 were protected from glutamate adverse effects in a statistically significant manner. In panel B, the effect of compound SRI22818 on NMDA induced neurotoxicity is shown. Primary neurons were exposed to the compound SRI 22818 at 3 μM for 36 hours prior to NMDA toxicity and were present during the following incubation prior to quantification of cell viability. NMDA exposure lasted 1 hour. Compound SRI22818 did not affect general viability but was able to decrease NMDA toxicity by 50% in a statistically significant manner. Finally, compound SRI22818 also was tested for its effect on β-Amyloid toxicity. β-amyloid(1-42) at 20 μM was used in these experiments in its fibrillar form. Fibrillar amyloid was obtained accordingly to manufacturer instructions by preincubating the agent at 370° C. in an ad hoc saline solution for 48 hours prior to the experiments. Fibrillar amyloid caused significant neuronal death over the 24 hour incubation, as quantified via multiple image-based and biochemical assays. Neurons were pre-exposed to 3 μM SRI22818, or vehicle, for 1 hour prior to exposure to amyloid and present throughout the incubation with the toxin. SRI22818 completely prevented fibrillar amyloid toxic effect, a very promising result.

Formulations

Compounds of the present disclosure can be administered by any conventional means available for use in conjunction with pharmaceuticals, either as individual therapeutic agents or in a combination of therapeutic agents. They can be administered alone, but generally administered with a pharmaceutical carrier selected on the basis of the chosen route of administration and standard pharmaceutical practice. The compounds can also be administered in conjunction with other therapeutic agents if desired.

The pharmaceutically acceptable carriers described herein, for example, vehicles, adjuvants, excipients, or diluents, are well-known to those who are skilled in the art. Typically, the pharmaceutically acceptable carrier is chemically inert to the active compounds and has no detrimental side effects or toxicity under the conditions of use. The pharmaceutically acceptable carriers can include polymers and polymer matrices.

The compounds of this disclosure can be administered by any conventional method available for use in conjunction with pharmaceuticals, either as individual therapeutic agents or in a combination of therapeutic agents.

The dosage administered will, of course, vary depending upon known factors, such as the pharmacodynamic characteristics of the particular agent and its mode and route of administration; the age, health and weight of the recipient; the nature and extent of the symptoms; the kind of concurrent treatment; the frequency of treatment; and the effect desired. A daily dosage of active ingredient can be expected to be about 0.001 to 1000 milligrams (mg) per kilogram (kg) of body weight, with the preferred dose being 0.1 to about 30 mg/kg.

Dosage forms (compositions suitable for administration) typically contain from about 1 mg to about 500 mg of active ingredient per unit. In these pharmaceutical compositions, the active ingredient will ordinarily be present in an amount of about 0.5-95% weight based on the total weight of the composition.

The active ingredient can be administered orally in solid dosage forms, such as capsules, tablets, and powders, or in liquid dosage forms, such as elixirs, syrups and suspensions. It can also be administered parenterally, in sterile liquid dosage forms. The active ingredient can also be administered intranasally (nose drops) or by inhalation of a drug powder mist. Other dosage forms are potentially possible such as administration transdermally, via patch mechanism or ointment.

Formulations suitable for oral administration can consist of (a) liquid solutions, such as an effective amount of the compound dissolved in diluents, such as water, saline, or orange juice; (b) capsules, sachets, tablets, lozenges, and troches, each containing a predetermined amount of the active ingredient, as solids or granules; (c) powders; (d) suspensions in an appropriate liquid; (e) suitable emulsions; and long acting or delayed release formulations. Liquid formulations may include diluents, such as water and alcohols, for example, ethanol, benzyl alcohol, propylene glycol, glycerin, and the polyethylene alcohols, either with or without the addition of a pharmaceutically acceptable surfactant, suspending agent, or emulsifying agent. Capsule forms can be of the ordinary hard- or soft-shelled gelatin type containing, for example, surfactants, lubricants, and inert fillers, such as lactose, sucrose, calcium phosphate, and corn starch. Tablet forms can include one or more of the following: lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible carriers. Lozenge forms can comprise the active ingredient in a flavor, usually sucrose and acacia or tragacanth, as well as pastilles comprising the active ingredient in an inert base, such as gelatin and glycerin, or sucrose and acadia, emulsions, and gels containing, in addition to the active ingredient, such carriers as are known in the art.

The compounds of the present disclosure, alone or in combination with other suitable components, can be made into aerosol formulations to be administered via inhalation. These aerosol formulations can be placed into pressurized acceptable propellants, such as dichlorodifluoromethane, propane, and nitrogen. They also may be formulated as pharmaceuticals for non-pressured preparations, such as in a nebulizer or an atomizer.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The compound can be administered in a physiologically acceptable diluent in a pharmaceutical carrier, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol such as poly(ethyleneglycol) 400, glycerol ketals, such as 2,2-dimethyl-1,3-dioxolane-4-methanol, ethers, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils, which can be used in parenteral formulations include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters. Suitable soaps for use in parenteral formulations include fatty alkali metal, ammonium, and triethanolamine salts, and suitable detergents include (a) cationic detergents such as, for example, dimethyldialkylammonium halides, and alkylpyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylene polypropylene copolymers, (d) amphoteric detergents such as, for example, alkyl β-aminopropionates, and 2-alkylimidazoline quaternary ammonium salts, and (e) mixtures thereof.

The parenteral formulations typically contain from about 0.5% to about 25% by weight of the active ingredient in solution. Suitable preservatives and buffers can be used in such formulations. In order to minimize or eliminate irritation at the site of injection, such compositions may contain one or more nonionic surfactants having a hydrophile-lipophile balance (HLB) of from about 12 to about 17. The quantity of surfactant in such formulations ranges from about 5% to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol.

Pharmaceutically acceptable excipients are also well-known to those who are skilled in the art. The choice of excipient will be determined in part by the particular compound, as well as by the particular method used to administer the composition. Accordingly, there is a wide variety of suitable formulations of the pharmaceutical composition of the present disclosure. The following methods and excipients are merely exemplary and are in no way limiting. The pharmaceutically acceptable excipients preferably do not interfere with the action of the active ingredients and do not cause adverse side-effects. Suitable carriers and excipients include solvents such as water, alcohol, and propylene glycol, solid absorbants and diluents, surface active agents, suspending agent, tableting binders, lubricants, flavors, and coloring agents.

The formulations can be presented in unit-dose or multi-dose sealed containers, such as ampoules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets. The requirements for effective pharmaceutical carriers for injectable compositions are well known to those of ordinary skill in the art. See *Pharmaceutics and Pharmacy Practice*, J.B. Lippincott Co., Philadelphia, Pa., Banker and Chalmers, Eds., 238-250 (1982) and *ASHP Handbook on Injectable Drugs*, Toissel, 4th ed., 622-630 (1986).

Formulations suitable for topical administration include lozenges comprising the active ingredient in a flavor, usually sucrose and acacia or tragacanth; pastilles comprising the active ingredient in an inert base, such as gelatin and glycerin, or sucrose and acacia; and mouthwashes comprising the active ingredient in a suitable liquid carrier; as well as creams, emulsions, and gels containing, in addition to the active ingredient, such carriers as are known in the art.

Additionally, formulations suitable for rectal administration may be presented as suppositories by mixing with a variety of bases such as emulsifying bases or water-soluble bases. Formulations suitable for vaginal administration may be presented as pessaries, tampons, creams, gels, pastes, foams, or spray formulas containing, in addition to the active ingredient, such carriers as are known in the art to be appropriate.

Suitable pharmaceutical carriers are described in Remington's Pharmaceutical Sciences, Mack Publishing Company, a standard reference text in this field.

The dose administered to an animal, particularly a human, in the context of the present disclosure should be sufficient to affect a therapeutic response in the animal over a reasonable time frame. One skilled in the art will recognize that dosage will depend upon a variety of factors including a condition of the animal, the body weight of the animal, as well as the severity and stage of the condition being treated.

A suitable dose is that which will result in a concentration of the active agent in a patient which is known to affect the desired response. The preferred dosage is the amount which results in maximum inhibition of the condition being treated, without unmanageable side effects.

The size of the dose also will be determined by the route, timing and frequency of administration as well as the existence, nature, and extend of any adverse side effects that might accompany the administration of the compound and the desired physiological effect.

Useful pharmaceutical dosage forms for administration of the compounds according to the present disclosure can be illustrated as follows:

Hard Shell Capsules

A large number of unit capsules are prepared by filling standard two-piece hard gelatine capsules each with 100 mg of powdered active ingredient, 150 mg of lactose, 50 mg of cellulose and 6 mg of magnesium stearate.

Soft Gelatin Capsules

A mixture of active ingredient in a digestible oil such as soybean oil, cottonseed oil or olive oil is prepared and injected by means of a positive displacement pump into molten gelatin to form soft gelatin capsules containing 100 mg of the active ingredient. The capsules are washed and dried. The active ingredient can be dissolved in a mixture of polyethylene glycol, glycerin and sorbitol to prepare a water miscible medicine mix.

Tablets

A large number of tablets are prepared by conventional procedures so that the dosage unit was 100 mg of active ingredient, 0.2 mg. of colloidal silicon dioxide, 5 mg of magnesium stearate, 275 mg of microcrystalline cellulose, 11 mg. of starch, and 98.8 mg of lactose. Appropriate aqueous and non-aqueous coatings may be applied to increase palatability, improve elegance and stability or delay absorption.

Solid oral dosage forms may be made by conventional and novel processes. These units are taken orally without water for immediate dissolution and delivery of the medication. The active ingredient is mixed in a liquid containing ingredient such as sugar, gelatin, pectin and sweeteners. These liquids are solidified into solid tablets or caplets by freeze drying and solid state extraction techniques. The drug compounds may be compressed with viscoelastic and thermoelastic sugars and polymers or effervescent components to produce porous matrices intended for immediate release, without the need of water.

Long-Acting or Delayed Release Formulations can be made by conventional and novel processes, which provide for the release of the active compound over a extended period of time. For example, the delayed release formulation can be prepared as an oral dosage form that passes through the stomach intact and dissolved in the small intestine or an injectible formulation that provides for the sustained release of the active compound into the blood stream over an extended period of time. Moreover, these type of formulations can be, for example, in the form of an emulsion, suspension, solution, and/or an enteric coated tablet or capsule.

Moreover, the compounds of the present disclosure can be administered in the form of nose drops, or metered dose and a nasal or buccal inhaler. The drug is delivered from a nasal solution as a fine mist or from a powder as an aerosol.

The term "comprising" (and its grammatical variations) as used herein is used in the inclusive sense of "having" or "including" and not in the exclusive sense of "consisting only of." The terms "a" and "the" as used herein are understood to encompass the plural as well as the singular.

The term "patient" or "subject" means an animal (e.g., cow, horse, sheep, pig, chicken, turkey, quail, cat, dog, mouse, rat, rabbit, guinea pig, etc.) or a mammal, including chimeric and transgenic animals and mammals. In one embodiment, the term "patient" or "subject" means a monkey or a human, most preferably a human. In certain embodiments, the patient is a human infant, child, adolescent, adult, or geriatric patient. In a particular embodiment, the patient is a healthy individual, e.g., an individual not displaying symptoms of memory impairment or not suffering from a neurodegenerative disease.

All publications, patents and patent applications cited in this specification are herein incorporated by reference, and for any and all purpose, as if each individual publication, patent or patent application were specifically and individually indicated to be incorporated by reference. In the case of inconsistencies, the present disclosure will prevail.

The foregoing description of the disclosure illustrates and describes the present disclosure. Additionally, the disclosure shows and describes only the preferred embodiments but, as mentioned above, it is to be understood that the disclosure is capable of use in various other combinations, modifications, and environments and is capable of changes or modifications within the scope of the concept as expressed herein, commensurate with the above teachings and/or the skill or knowledge of the relevant art.

The embodiments described hereinabove are further intended to explain best modes known of practicing it and to enable others skilled in the art to utilize the disclosure in such, or other, embodiments and with the various modifications required by the particular applications or uses. Accordingly, the description is not intended to limit it to the form disclosed herein. Also, it is intended that the appended claims be construed to include alternative embodiments.

What is claimed is:

1. A method for enhancing memory comprising administering to a patient that is predisposed to developing a neurodegenerative disease a memory enhancing amount of the following compound:

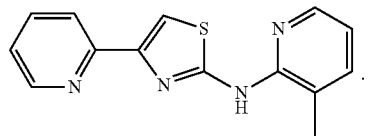 [SMILES: Cc1cccnc1Nc1nc(-c2ccccn2)cs1]

2. A method for minimizing the decline of memory comprising administering to a patient that is predisposed to developing a neurodegenerative disease, an effective amount of the following compound:

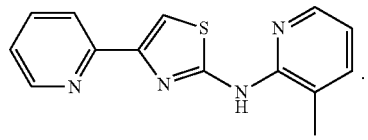 [SMILES: Cc1cccnc1Nc1nc(-c2ccccn2)cs1]

3. A method for improving or maintaining baseline memory comprising administering to a patient that is predisposed to developing a neurodegenerative disease an effective amount of the following compound:

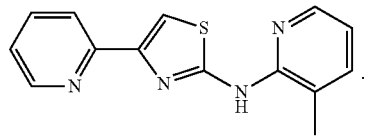 [SMILES: Cc1cccnc1Nc1nc(-c2ccccn2)cs1]

4. A method for enhancing memory comprising administering to a patient that is suffering from a neurodegenerative disease a memory enhancing amount of the following compound:

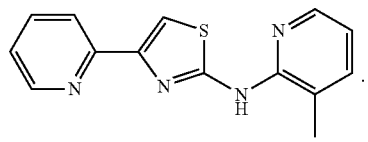 [SMILES: Cc1cccnc1Nc1nc(-c2ccccn2)cs1]

5. A method for minimizing the decline of memory comprising administering to a patient that is suffering from a neurodegenerative disease an effective amount of the following compound:

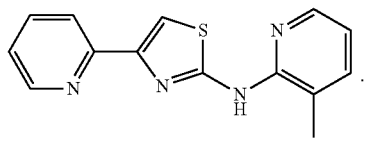 [SMILES: Cc1cccnc1Nc1nc(-c2ccccn2)cs1]

6. A method for improving or maintain baseline memory comprising administering to patient that is suffering from a neurodegenerative disease an effective amount of the following compound:

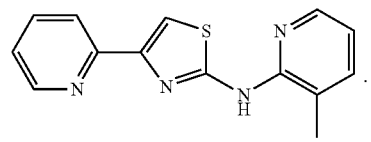 [SMILES: Cc1cccnc1Nc1nc(-c2ccccn2)cs1]

* * * * *